(12) United States Patent
Meade et al.

(10) Patent No.: US 9,796,982 B2
(45) Date of Patent: *Oct. 24, 2017

(54) USE OF CRY1DA IN COMBINATION WITH CRY1CA FOR MANAGEMENT OF RESISTANT INSECTS

(75) Inventors: Thomas Meade, Zionsville, IN (US); Kenneth Narva, Zionsville, IN (US); Nicholas P. Storer, Kensington, MD (US); Joel J. Sheets, Zionsville, IN (US); Aaron T. Woosley, Fishers, IN (US); Stephanie L. Burton, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 625 days.

This patent is subject to a terminal disclaimer.

(21) Appl. No.: 13/516,663

(22) PCT Filed: Dec. 16, 2010

(86) PCT No.: PCT/US2010/060828
§ 371 (c)(1),
(2), (4) Date: Sep. 7, 2012

(87) PCT Pub. No.: WO2011/084629
PCT Pub. Date: Jul. 14, 2011

(65) Prior Publication Data
US 2013/0007923 A1  Jan. 3, 2013

Related U.S. Application Data

(60) Provisional application No. 61/284,281, filed on Dec. 16, 2009, provisional application No. 61/284,275, filed on Dec. 16, 2009, provisional application No. 61/284,252, filed on Dec. 16, 2009.

(51) Int. Cl.
*C12N 15/82* (2006.01)
*A01N 63/02* (2006.01)

(52) U.S. Cl.
CPC ......... *C12N 15/8286* (2013.01); *A01N 63/02* (2013.01)

(58) Field of Classification Search
None
See application file for complete search history.

(56) References Cited

U.S. PATENT DOCUMENTS

| 5,188,960 A | 2/1993 | Payne et al. |
| 5,273,746 A | 12/1993 | Payne et al. |
| 5,593,881 A | 1/1997 | Thompson et al. |
| 5,866,784 A * | 2/1999 | Van Mellaert et al. ...... 800/302 |
| 6,603,063 B1 * | 8/2003 | Feitelson ............... A01N 63/00 435/252.3 |
| 2004/0197916 A1 | 10/2004 | Carozzi et al. |
| 2005/0155103 A1 | 7/2005 | Baum et al. |
| 2008/0311096 A1 | 12/2008 | Lang et al. |
| 2010/0269223 A1 | 10/2010 | Lira et al. |
| 2011/0047646 A1 | 2/2011 | Manzanero et al. |

FOREIGN PATENT DOCUMENTS

| CN | 101405296 | 4/2009 |
| EP | 024626 | 12/1990 |
| WO | WO 2007/107302 A2 | 9/2007 |
| WO | WO 2009/132850 | 5/2009 |
| WO | WO 2011/075587 | 6/2011 |
| WO | WO 2011/075588 | 6/2011 |
| WO | WO 2011/084630 | 7/2011 |
| WO | WO 2011/084634 | 7/2011 |

OTHER PUBLICATIONS

Crickmore et al (2014 "*Bacillus thuringiensis* toxin nomenclature" http://www.btnomenclature.info/).*
Bates et al (2005, Nature Biotechnol. 23:57-62).*
Hernández-Martinez et al (Mar. 2008, J. Invert. Pathol. 97:245-250).*
Monnerat et al (2006, Appl. Environ. Microbiol. 72:7029-7035).*
Rang et al (2004, Current Microbiol. 49:22-27).*
Lee et al (2006, Biochem. Biophys. Res. Comm. 339:1043-1047).*
Crickmore et al (2015 "*Bacillus thuringiensis* toxin nomenclature" http://www.lifesci.sussex.ac.uk/home/Neil_Crickmore/Bt/vip.html).*
Luo et al (1999, Appl. Environ. Microbiol. 65:457-464).*
Jan. 1, 2009, XP55060016, Retrieved from the Internet: URL:http://www.agry.purdue.edu/CCA/2008/Proceedings/Steffey.pdf;
Retrieved on Apr. 11, 2013 (*Insect Resistance Management*).
Jan. 1, 2006, XP55060066, Retrieved from the Internet: URL:http://www.agry.purdue.edu/CCA/2008/Proceedings/Steffey.pdf;
retrieved on Apr. 17, 2013 (*abstract).
Perlak, Frederick, J. et al., "Development and commercial use of Bollgard(R) cotton in the USA: Early promises versus today's reality", The Plant Journal, Blackwell Scientific Publications, Oxford, GB, vol. 27, No. 6, Sep. 1, 2001, pp. 489-501, XP002332979, ISSN: 0960-7412, DOI: 10.1046/J.1365-313X.2001.01120.X (*abstract, table 1 and conclusion*).
Pittendrigh, B. R. et al., "Active refuges can inhibit the evolution of resistane in insect towards transgenic insect-resistant plants", Journal of Theoretical Biology, Academic Press, London, GB, vol. 231, No. 4, Dec. 21, 2004, pp. 461-474, XP004635702, ISSN: 0022-5193, DOI: 10.1016/J.JTBI.2004.05.023 (*Abstract, figure 1, paragraph [03.4] and [03.7].
Dec. 1, 2009, XP55060013, Retrieved from the Internet: URL;http://combat-monsanto.org/IMG/pdf/btcrops.pdf, retrieved on Apr. 17, 2013, (*abstract, table 1-5, resistance management theory, refuges high doses, and pyramiding; figures 1, 2.

(Continued)

*Primary Examiner* — Anne Kubelik
(74) *Attorney, Agent, or Firm* — Ronald S. Maciak; Barnes & Thornburg LLP

(57) ABSTRACT

The subject invention includes methods and plants for controlling fall armyworm lepidopteran insects, said plants comprising a Cry1Da insecticidal protein and a Cry1Ca insecticidal protein, and various combinations of other proteins comprising this pair of proteins, to delay or prevent development of resistance by the insects.

18 Claims, 1 Drawing Sheet

(56) References Cited

OTHER PUBLICATIONS

Dec. 9, 2008. XP55060010, DOI: 10.1094/PHP-2004, Retrieved from the Internet: URL:http://www.pnas.org/content/105/49/19029.full.pdf#page=1&view=FitH, retrieved on Apr. 17, 2013] (*whole doc.).
Insecticidal protein Cry1Ca (*Bacillus thuringiensis*), Accession No. AAM00264.1, Chen, Z. et al., GENBANK, Apr. 2, 2002.
Gutierrez, et al. Pysiologically based demographis of Bt cotton-pest interactions I. Pink bollworm resistance, refuge and risk, Andrew Paul Gutierrez, et al., Ecological Modeling, 2006, vol. 191, pp. 346-359, published on Dec. 31, 2006.
Swiecicka, et al. Novel Isolate of *Bacillus thuringiensis* subsp. Thurinviensis That Produces a Quasicuboidal Crystal of Cry1Ab21 Toxic to Larae of Trichoplusia ni, Izabela Swiecicka, et al., Applied and Environmental Microbiology, vol. 74, No. 4, published on Feb. 28, 2008.
Manyangarirwa, W. et al., Gene pyramiding as a Bt resistance management strategy: Howe sustainable is this strategy?, African Journal of Biotechnology vol. 5 (10), pp. 781-785, May 16, 2006.
Tabashnik B. E. et al., Field—Evolved Insect Resistance to Bt Crops: Definition, Theory, and Data, Journal of Economic Entomology, vol. 102 (6), pp. 2011-2025 (2009), available at http://combat-monsanto.org/IMG/pdf/btcrops.pdf.
Bravo A. et al., How to cope with insect resistance to Bt toxins?, Trends in Biotechnology, vol. 26 (10), pp. 573-579 (2008).
Chitkowski R L et al: "Field and Laboratory Evaluations of Transgenic Cottons Expressing One or Two Bacillus Thuringiensis Var. Kurstaki Berliner Proteins for Management of Noctuid (Lepidoptera) Pests", Journal of Economic Entomology, Entomological Society of America, Landham, Landham,MD,US, vol. 96, No. 3, Jun. 1, 2003 (Jun. 1, 2003), pp. 755-762, XP008052475, ISSN: 0022-0493.

Zhao J. Z. et al: "Concurrent use of transgenic plants expressing a single and two *Bacillus thuringiensis* genes speeds insect adaptation to pyramided plants", Proceedings of the National Academy of Sciences, vol. 102, No. 24, Jun. 14, 2005 (Jun. 14, 2005), pp. 8426-8430, XP55185196, ISSN: 0027-8424, DOI: 1 0.1 073/pnas.04093241 02.

Jurat-Fuentes J Let Al: "Dual Resistance to Bacillus Thuringiensis Cry1Ac and CRY2AA Toxins in Heliothis Virescens Suggests Multiple Mechanisms of Resistance", Applied and Environmental Microbiology, American Society for Microbiology, US, vol. 69, No. 10, Oct. 1, 2003 (Oct. 1, 2003), pp. 5898-5906, XP001196935, ISSN: 0099-2240, DOI: 1 0.1128/AEM.69.1 0.5898-5906.2003.

Zhao J-Z et al: "Transgenic plants expressing two *Bacillus thuringiensis* toxins delay insect resistance evolution", Nature Biotechnology, Nature Publishing Group, US, Dec. 1, 2003 (Dec. 1, 2003), pp. 1493-1497, XP002344666, ISSN: 1087-0156, DOI: 10.1038/NBT907.

Sauka, Bacillus Thringiensis:Generalidades.Un Acercamiento a Su Empleo En El Biocontrol, hereinafter remarks, Revista Argentina de Microbiologia, 2008, V40, p. 124-140, De Insectos Lepidopteros Que Son Plagas Agricolas.

Luo, K. et al., Toxicity, binding, and permeability analyses of four *Bacillus thuringiensis* Cry1 delta-endotoxins using brush border membrane vesicles of *Spodoptera exigua* and *Spodoptera frugiperda*., Appl. Environ. Microbiol., 1999, vol. 65 No. 2, pp. 457-464.

de Maagd et al., "*Bacillus thuringiensis* Delta-Endotoxin Cry1C Domain III Can Function as a Specificity Determinant for Spodoptera exigua in Different, but Not All, Cry1-Cry1C Hybrids," Appl. Environ. Microbiol. vol. 66 No. 4, pp. 1559-1563 (2000).

Pakula et al., Genetic analysis of protein stability and function, Anna. Rev. Genet., vol. 23, p. 289-310 (1989).

Roush, "Two-toxin strategies for management of insecticidal transgenic crops: can pyraminding succeed where pesticide mixtures have not?", Phil. Trans. R. Soc. Lond. B, 353: 1777-1786 (1998).

Tabashnik, "One gene in diamondback moth confers resistance to four *Bacillus thuringiensis* toxins," PNAS, 94:1640-1644 (1997).

* cited by examiner

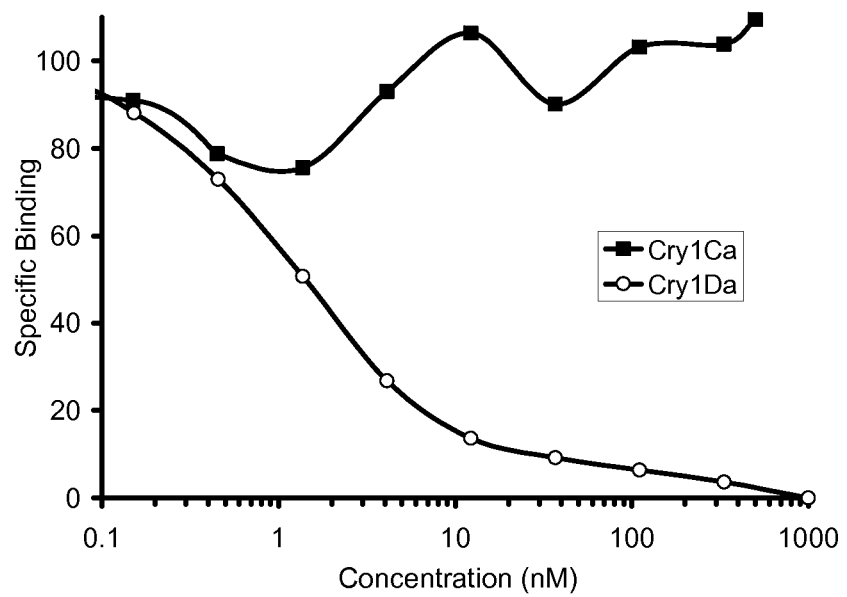

SEQUENCE LISTING

<160> NUMBER OF SEQ ID NOS: 2

<210> SEQ ID NO 1
<211> LENGTH: 619
<212> TYPE: PRT
<213> ORGANISM: Artificial Sequence
<220> FEATURE:
<223> OTHER INFORMATION: Cry1Ca

<400> SEQUENCE: 1

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
```

```
            260                 265                 270

Ile Asn Phe Asn Pro Gln Leu Gln Ser Val Ala Gln Leu Pro Thr Phe
            275                 280                 285

Asn Val Met Glu Asn Ser Ala Ile Arg Asn Pro His Leu Phe Asp Ile
        290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr
    610                 615

<210> SEQ ID NO 2
<211> LENGTH: 594
<212> TYPE: PRT
<213> ORGANISM: Artificial Sequence
<220> FEATURE:
<223> OTHER INFORMATION: Cry1Da

<400> SEQUENCE: 2

Met Glu Ile Asn Asn Gln Asn Gln Cys Val Pro Tyr Asn Cys Leu Ser
```

```
1               5                    10                   15
Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
            35                  40                  45

Phe Val Pro Gly Gly Phe Ile Val Gly Leu Leu Glu Leu Ile Trp
            50              55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
            115                 120                 125

Met Arg Ile Gln Phe Asn Asp Met Asn Ser Ala Leu Ile Thr Ala Ile
            130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
            195                 200                 205

Thr Tyr Asn Gln Gly Leu Arg Arg Leu Glu Gly Arg Phe Leu Ser Asp
210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Ser Tyr Pro Thr Phe Ser Ala
            275                 280                 285

Ala Glu Ser Ala Ile Ile Arg Ser Pro His Leu Val Asp Phe Leu Asn
            290                 295                 300

Ser Phe Thr Ile Tyr Thr Asp Ser Leu Ala Arg Tyr Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Pro Val Thr
            340                 345                 350

Ile Thr Ala Ser Pro Ser Val Pro Ile Phe Arg Thr Leu Ser Tyr Ile
            355                 360                 365

Thr Gly Leu Asp Asn Ser Asn Pro Val Ala Gly Ile Glu Gly Val Glu
            370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
            405                 410                 415

Ile Gly Tyr Ser His Arg Leu Cys His Ala Thr Phe Leu Glu Arg Ile
            420                 425                 430
```

-continued

```
Ser Gly Pro Arg Ile Ala Gly Thr Val Phe Ser Trp Thr His Arg Ser
        435                 440                 445
Ala Ser Pro Thr Asn Glu Val Ser Pro Ser Arg Ile Thr Gln Ile Pro
        450                 455                 460
Trp Val Lys Ala His Thr Leu Ala Ser Gly Ala Ser Val Ile Lys Gly
465                 470                 475                 480
Pro Gly Phe Thr Gly Gly Asp Ile Leu Thr Arg Asn Ser Met Gly Glu
                485                 490                 495
Leu Gly Thr Leu Arg Val Thr Phe Thr Gly Arg Leu Pro Gln Ser Tyr
                500                 505                 510
Tyr Ile Arg Phe Arg Tyr Ala Ser Val Ala Asn Arg Ser Gly Thr Phe
            515                 520                 525
Arg Tyr Ser Gln Pro Pro Ser Tyr Gly Ile Ser Phe Pro Lys Thr Met
        530                 535                 540
Asp Ala Gly Glu Pro Leu Thr Ser Arg Ser Phe Ala His Thr Thr Leu
545                 550                 555                 560
Phe Thr Pro Ile Thr Phe Ser Arg Ala Gln Glu Glu Phe Asp Leu Tyr
                565                 570                 575
Ile Gln Ser Gly Val Tyr Ile Asp Arg Ile Glu Phe Ile Pro Val Thr
                580                 585                 590
Ala Thr
```

USE OF CRY1DA IN COMBINATION WITH CRY1CA FOR MANAGEMENT OF RESISTANT INSECTS

CROSS-REFERENCE TO RELATED APPLICATIONS

This is a national phase application, filed pursuant to 35 U.S.C. § 371, of PCT application No. PCT/US2010/060828, filed on Dec. 16, 2010, which claims the benefit of U.S. provisional application No. 61/284,281, filed on Dec. 16, 2009, and U.S. provisional application No. 61/284,275, filed on Dec. 16, 2009, and U.S. provisional application No. 61/284,252, filed on Dec. 16, 2009. The prior applications are incorporated herein by reference in their entirety.

BACKGROUND OF THE INVENTION

Humans grow corn for food and energy applications. Humans also grow many other crops, including soybeans and cotton. Insects eat and damage plants and thereby undermine these human efforts. Billions of dollars are spent each year to control insect pests and additional billions are lost to the damage they inflict. Synthetic organic chemical insecticides have been the primary tools used to control insect pests but biological insecticides, such as the insecticidal proteins derived from *Bacillus thuringiensis* (Bt), have played an important role in some areas. The ability to produce insect-resistant plants through transformation with Bt insecticidal protein genes has revolutionized modern agriculture and heightened the importance and value of insecticidal proteins and their genes.

Several Bt proteins have been used to create the insect-resistant transgenic plants that have been successfully registered and commercialized to date. These include Cry1Ab, Cry1Ac, Cry1F and Cry3Bb in corn, Cry1Ac and Cry2Ab in cotton, and Cry3A in potato.

The commercial products expressing these proteins express a single protein except in cases where the combined insecticidal spectrum of 2 proteins is desired (e.g., Cry1Ab and Cry3Bb in corn combined to provide resistance to lepidopteran pests and rootworm, respectively) or where the independent action of the proteins makes them useful as a tool for delaying the development of resistance in susceptible insect populations (e.g., Cry1Ac and Cry2Ab in cotton combined to provide resistance management for tobacco budworm). See also U.S. Patent Application Publication No. 2009/0313717, which relates to a Cry2 protein plus a Vip3Aa, Cry1F, or Cry1A for control of *Helicoverpa zea* or armigerain. WO 2009/132850 relates to Cry1F or Cry1A and Vip3Aa for controlling *Spodoptera frugiperda*. U.S. Patent Application Publication No. 2008/0311096 relates in part to Cry1Ab for controlling Cry1F-resistant ECB.

That is, some of the qualities of insect-resistant transgenic plants that have led to rapid and widespread adoption of this technology also give rise to the concern that pest populations will develop resistance to the insecticidal proteins produced by these plants. Several strategies have been suggested for preserving the utility of Bt-based insect resistance traits which include deploying proteins at a high dose in combination with a refuge, and alternation with, or co-deployment of, different toxins (McGaughey et al. (1998), "B.t. Resistance Management," *Nature Biotechnol.* 16:144-146).

The proteins selected for use in an insect resistant management (IRM) stack need to exert their insecticidal effect independently so that resistance developed to one protein does not confer resistance to the second protein (i.e., there is not cross resistance to the proteins). If, for example, a pest population that is resistant to "Protein A" is sensitive to "Protein B", one would conclude that there is not cross resistance and that a combination of Protein A and Protein B would be effective in delaying resistance to Protein A alone.

In the absence of resistant insect populations, assessments can be made based on other characteristics presumed to be related to mechanism of action and cross-resistance potential. The utility of receptor-mediated binding in identifying insecticidal proteins likely to not exhibit cross resistance has been suggested (van Mellaert et al. 1999). The key predictor of lack of cross resistance inherent in this approach is that the insecticidal proteins do not compete for receptors in a sensitive insect species.

In the event that two Bt toxins compete for the same receptor, then if that receptor mutates in that insect so that one of the toxins no longer binds to that receptor and thus is no longer insecticidal against the insect, it might be the case that the insect will also be resistant to the second toxin (which competitively bound to the same receptor). That is, the insect is said to be cross-resistant to both Bt toxins. However, if two toxins bind to two different receptors, this could be an indication that the insect would not be simultaneously resistant to those two toxins.

For example, Cry1Fa protein is useful in controlling many lepidopteran pests species including the European corn borer (ECB; *Ostrinia nubilalis* (Hubner)) and the fall armyworm (FAW; *Spodoptera frugiperda*), and is active against the sugarcane borer (SCB; *Diatraea saccharalis*). The Cry1Fa protein, as produced in transgenic corn plants containing event TC1507, is responsible for an industry-leading insect resistance trait for FAW control. Cry1Fa is further deployed in the Herculex®, SmartStax™, and WideStrike™ products.

Additional Cry toxins are listed at the website of the official B. t. nomenclature committee (Crickmore et al.; lifesci.sussex.ac.uk/home/Neil_Crickmore/Bt/). There are currently nearly 60 main groups of "Cry" toxins (Cry1-Cry59), with additional Cyt toxins and VIP toxins and the like. Many of each numeric group have capital-letter subgroups, and the capital letter subgroups have lower-cased letter sub-subgroups. (Cry1 has A-L, and Cry1A has a-i, for example).

BRIEF SUMMARY OF THE INVENTION

The subject invention relates in part to the surprising discovery that Cry1Da and Cry1Ca do not compete for binding sites in fall armyworm (FAW; *Spodoptera frugiperda*) gut cell membrane preparations. As one skilled in the art will recognize with the benefit of this disclosure, plants that produce both of these proteins (including insecticidal portions of the full-length proteins) can delay or prevent the development of resistance to any of these insecticidal proteins alone.

Thus, the subject invention relates in part to the use of a Cry1Da protein in combination with a Cry1Ca protein. Plants (and acreage planted with such plants) that produce both of these proteins are included within the scope of the subject invention.

The subject invention also relates in part to triple stacks or "pyramids" of three (or more) toxins, with Cry1Da and Cry1Ca being the base pair. In some preferred pyramid embodiments, the combination of the selected toxins provides non-cross-resistant action against FAW. Some preferred "three sites of action" pyramid combinations include the subject base pair of proteins plus Cry1Fa, Vip3Ab, Cry1Be, or Cry1E as the third protein for targeting FAW.

These particular triple stacks would, according to the subject invention, advantageously and surprisingly provide three sites of action against FAW. This can help to reduce or eliminate the requirement for refuge acreage.

Additional toxins/genes can also be added according to the subject invention. For example, if Cry1Fa or Cry1Be are stacked with the subject pair of proteins (both Cry1Fa and Cry1Be are both active against both FAW and European cornborer (ECB)), adding two additional proteins to this triple stack wherein the two added proteins target ECB, would provide three sites of action against FAW, and three sites of action against ECB. These two added proteins (the fourth and fifth proteins) could be selected from the group consisting of Cry2A, Cry1I, DIG-3, and Cry1Ab. This would result in a five-protein stack having three sites of action against two insects (ECB and FAW).

BRIEF DESCRIPTION OF THE FIGURES

FIG. 1 shows percent specific binding of $^{125}$I Cry1Da (0.5 nM) in BBMV's from FAW versus competition by unlabeled homologous Cry1Da (○) and heterologous CrylCa (■).

DETAILED DESCRIPTION OF THE INVENTION

The subject invention relates in part to the surprising discovery that Cry1Da and Cry1Ca do not compete for binding with each other in the gut of fall armyworms (FAW; *Spodoptera frugiperda*). Thus, a Cry1Da protein can be used in combination with a Cry1Ca protein in transgenic corn (and other plants; e.g., cotton and soybeans, for example) to delay or prevent FAW from developing resistance to either of these proteins alone. The subject pair of proteins can be effective at protecting plants (such as maize plants and/or soybean plants) from damage by Cry-resistant fall armyworm. That is, one use of the subject invention is to protect corn and other economically important plant species from damage and yield loss caused by fall armyworm populations that could develop resistance to Cry1Da or Cry1Ca.

The subject invention thus teaches an insect resistant management (IRM) stack comprising Cry1Da and Cry1Ca to prevent or mitigate the development of resistance by FAW to either or both of these proteins.

The present invention provides compositions for controlling lepidopteran pests comprising cells that produce a Cry1Da insecticidal protein and a Cry1Ca insecticidal protein.

The invention further comprises a host transformed to produce both a Cry1Da insecticidal protein and a Cry1Ca insecticidal protein, wherein said host is a microorganism or a plant cell. The subject polynucleotide(s) are preferably in a genetic construct under control of a non-Bacillus-thuringiensis promoter(s). The subject polynucleotides can comprise codon usage for enhanced expression in a plant.

It is additionally intended that the invention provides a method of controlling lepidopteran pests comprising contacting said pests or the environment of said pests with an effective amount of a composition that contains a Cry1Da core toxin-containing protein and further contains a Cry1Ca core toxin-containing protein.

An embodiment of the invention comprises a maize plant comprising a plant-expressible gene encoding a Cry1Ca insecticidal protein and a plant-expressible gene encoding a Cry1Da insecticidal protein, and seed of such a plant.

A further embodiment of the invention comprises a maize plant wherein a plant-expressible gene encoding a Cry1Ca insecticidal protein and a plant-expressible gene encoding a Cry1Da insecticidal protein have been introgressed into said maize plant, and seed of such a plant.

As described in the Examples, competitive receptor binding studies using radiolabeled Cry1Da protein show that the Cry1Ca protein does not compete for binding in FAW tissues to which Cry1Da binds. These results also indicate that the combination of Cry1Da and Cry1Ca proteins can be an effective means to mitigate the development of resistance in FAW populations to either of these proteins. Thus, based in part on the data described herein, it is thought that co-production (stacking) of the Cry1Ca and Cry1Da proteins can be used to produce a high dose IRM stack for FAW.

Other proteins can be added to this pair. For example, the subject invention also relates in part to triple stacks or "pyramids" of three (or more) toxins, with Cry1Da and Cry1Ca being the base pair. In some preferred pyramid embodiments, the selected toxins have three separate sites of action against FAW. Some preferred "three sites of action" pyramid combinations include the subject base pair of proteins plus Cry1Fa, Vip3Ab, Cry1Be, or Cry1E as the third protein for targetting FAW. By "separate sites of action," it is meant any of the given proteins do not cause cross-resistance with each other. These particular triple stacks would, according to the subject invention, advantageously and surprisingly provide three sites of action against FAW. This can help to reduce or eliminate the requirement for refuge acreage.

Additional toxins/genes can also be added according to the subject invention. For example, if Cry1Fa or Cry1Be are stacked with the subject pair of proteins (both Cry1Fa and Cry1Be are both active against both FAW and European cornborer (ECB)), adding two additional proteins to this triple stack wherein the two added proteins target ECB, would provide three sites of action against FAW, and three sites of action against ECB. These two added proteins (the fourth and fifth proteins) could be selected from the group consisting of Cry2A, Cry1I, DIG-3 (see U.S. Patent Application Ser. No. 61/284,278 (filed Dec. 16, 2009) and US 2010 00269223), and Cry1Ab. This would result in a five-protein stack having three sites of action against two insects (ECB and FAW)

Thus, one deployment option is to use the subject pair of proteins in combination with a third toxin/gene, and to use this triple stack to mitigate the development of resistance in FAW to any of these toxins. Accordingly, the subject invention also relates in part to triple stacks or "pyramids" of three (or more) toxins. In some preferred pyramid embodiments, the selected toxins have three separate sites of action against FAW.

Included among deployment options of the subject invention would be to use two, three, or more proteins of the subject proteins in crop-growing regions where FAW can develop resistant populations.

For use of Cry1Fa plus Cry1C, see U.S. Patent Application Ser. No. 61/284,281 (filed Dec. 16, 2009), which shows that Cry1C is active against Cry1F-resistant FAW. For use of Cry1Fa plus Cry1D, see U.S. Patent Application Ser. No. 61/284,252 (filed Dec. 16, 2009), which shows that Cry1D is active against Cry1F-resistant FAW. These two applications also show that Cry1C does not compete with Cry1F for binding in FAW membrane preparations, and that Cry1D does not compete with Cry1F for binding in FAW membrane preparations. With Cry1Fa being active against FAW and ECB, Cry1Da plus Cry1Ca plus Cry1Fa would, according to the subject invention, advantageously and surprisingly provide three sites of action against FAW. This can help to reduce or eliminate the requirement for refuge acreage.

Cry1Fa is deployed in the Herculex®, SmartStax™, and WidesStrike™ products. The subject pair of genes (Cry1Da and Cry1Ca) could be combined into, for example, a Cry1Fa product such as Herculex®, SmartStax™, and WideStrike™. Accordingly, the subject pair of proteins could be significant in reducing the selection pressure on these andother proteins. The subject pair of proteins could thus be used as in the three gene combinations for corn and other plants (cotton and soybeans, for example).

As discussed above, additional toxins/genes can also be added according to the subject invention. For the use of Cry1E (for controlling FAW), see U.S. Patent Application Ser. No. 61/284,278 (filed Dec. 16, 2009). For use of Cry1Ab (for controlling ECB), see U.S. Patent Application Publication No. 2008/0311096.

Plants (and acreage planted with such plants) that produce any of the subject combinations of proteins are included within the scope of the subject invention. Additional toxins/genes can also be added, but the particular stacks discussed above advantageously and surprisingly provide multiple sites of action against FAW and/or ECB. This can help to reduce or eliminate the requirement for refuge acreage. A field thus planted of over ten acres is thus included within the subject invention.

GENBANK can also be used to obtain the sequences for any of the genes and proteins disclosed or mentioned herein. See Appendix A, below. Relevant sequences are also available in patents. For example, U.S. Pat. No. 5,188,960 and U.S. Pat. No. 5,827,514 describe Cry1Fa core toxin containing proteins suitable for use in carrying out the present invention. U.S. Pat. No. 6,218,188 describes plant-optimized DNA sequences encoding Cry1Fa core toxin-containing proteins that are suitable for use in the present invention.

Combinations of proteins described herein can be used to control lepidopteran pests. Adult lepidopterans, for example, butterflies and moths, primarily feed on flower nectar and are a significant effector of pollination. Nearly all lepidopteran larvae, i.e., caterpillars, feed on plants, and many are serious pests. Caterpillars feed on or inside foliage or on the roots or stem of a plant, depriving the plant of nutrients and often destroying the plant's physical support structure. Additionally, caterpillars feed on fruit, fabrics, and stored grains and flours, ruining these products for sale or severely diminishing their value. As used herein, reference to lepidopteran pests refers to various life stages of the pest, including larval stages.

Some chimeric toxins of the subject invention comprise a full N-terminal core toxin portion of a Bt toxin and, at some point past the end of the core toxin portion, the protein has a transition to a heterologous protoxin sequence. The N-terminal, insecticidally active, toxin portion of a Bt toxin is referred to as the "core" toxin. The transition from the core toxin segment to the heterologous protoxin segment can occur at approximately the toxin/protoxin junction or, in the alternative, a portion of the native protoxin (extending past the core toxin portion) can be retained, with the transition to the heterologous protoxin portion occurring downstream.

As an example, one chimeric toxin of the subject invention, is a full core toxin portion of Cry1Da (roughly the first 600 amino acids) and/or a heterologous protoxin (the remaining amino acids to the C-terminus). In one preferred embodiment, the portion of a chimeric toxin comprising the protoxin is derived from a Cry1Ab protein toxin. In a preferred embodiment, the portion of a chimeric toxin comprising the protoxin is derived from a Cry1Ab protein toxin.

A person skilled in this art will appreciate that Bt toxins, even within a certain class such as Cry1Ca, will vary to some extent in length and the precise location of the transition from core toxin portion to protoxin portion. Typically, the Cry1Ca toxins are about 1150 to about 1200 amino acids in length. The transition from core toxin portion to protoxin portion will typically occur at between about 50% to about 60% of the full length toxin. The chimeric toxin of the subject invention will include the full expanse of this N-terminal core toxin portion. Thus, the chimeric toxin will comprise at least about 50% of the full length of the Cry1Bt toxin protein. This will typically be at least about 590 amino acids. With regard to the protoxin portion, the full expanse of the Cry1Ab protoxin portion extends from the end of the core toxin portion to the C-terminus of the molecule.

Genes and toxins. The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

As used herein, the boundaries represent approximately 95% (Cry1Da's and Cry1Ca's), 78% (Cry1D's and Cry1C's), and 45% (Cry1's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813. These cut offs can also be applied to the core toxins only.

It should be apparent to a person skilled in this art that genes encoding active toxins can be identified and obtained through several means. The specific genes or gene portions exemplified herein may be obtained from the isolates deposited at a culture depository. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Genes that encode active fragments may also be obtained using a variety of restriction enzymes. Proteases may be used to directly obtain active fragments of these protein toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments of genes encoding proteins that retain pesticidal activity are also included in this definition.

A further method for identifying the genes encoding the toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) DNA Probes, Stockton Press, New York, N.Y., pp. 169-170. Some examples of salt concentrations and temperature combinations are as follows (in order of increasing stringency): 2×SSPE or SSC at room temperature; 1X SSPE or SSC at 42° C.; 0.1×SSPE or SSC at 42° C.; 0.1×SSPE or SSC at 65° C. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Variant toxins. Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Below is a listing of examples of amino acids belonging to each class.

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant hosts. The genes encoding the toxins of the subject invention can be introduced into a wide variety of microbial or plant hosts. Expression of the toxin gene results, directly or indirectly, in the intracellular production and maintenance of the pesticide. Conjugal transfer and recombinant transfer can be used to create a Bt strain that expresses both toxins of the subject invention. Other host organisms may also be transformed with one or both of the toxin genes then used to accomplish the synergistic effect. With suitable microbial hosts, e.g., *Pseudomonas*, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the Bt toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobactenum, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobactenium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of methods is available for introducing a Bt gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. *Bacillus thuringiensis* or recombinant cells expressing the Bt toxins can be treated to prolong the toxin activity and stabilize the cell. The pesticide microcapsule that is formed comprises the Bt toxin or toxins within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene or genes, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will cross-link proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene or genes into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene or genes may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells producing the toxins of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores, crystals, and toxins of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., foliage or soil, by spraying, dusting, sprinkling, or the like.

Plant transformation. A preferred recombinant host for production of the insecticidal proteins of the subject invention is a transformed plant. Genes encoding Bt toxin proteins, as disclosed herein, can be inserted into plant cells using a variety of techniques which are well known in the art. For example, a large number of cloning vectors comprising a replication system in *Escherichia coli* and a marker that permits selection of the transformed cells are available for preparation for the insertion of foreign genes into higher plants. The vectors comprise, for example, pBR322, pUC series, M13 mp series, pACYC184, inter alia. Accordingly, the DNA fragment having the sequence encoding the Bt toxin protein can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516, Lee and Gelvin (2008), Hoekema (1985), Fraley et al., (1986), and An et al., (1985), and is well established in the art.

Once the inserted DNA has been integrated in the plant genome, it is relatively stable. The transformation vector normally contains a selectable marker that confers on the transformed plant cells resistance to a biocide or an antibiotic, such as Bialaphos, Kanamycin, G418, Bleomycin, or Hygromycin, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the Right and Left T-DNA border regions. They can be transformed directly into *Agrobacteria* (Holsters et al., 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. While some truncated toxins are exemplified herein, it is well-known in the Bt art that 130 kDa-type (full-length) toxins have an N-terminal half that is the core toxin, and a C-terminal half that is the protoxin "tail." Thus, appropriate "tails" can be used with truncated/core toxins of the subject invention. See e.g. U.S. Pat. No. 6,218,188 and U.S. Pat. No. 6,673,990. In addition, methods for creating synthetic Bt genes for use in plants are known in the art (Stewart and Burgin, 2007). One non-limiting example of a preferred transformed plant is a fertile maize plant comprising a plant expressible gene encoding a Cry1Da protein, and further comprising a second plant expressible gene encoding a Cry1Ca protein.

Transfer (or introgression) of the Cry1Da- and Cry1Ca-determined trait(s) into inbred maize lines can be achieved by recurrent selection breeding, for example by backcrossing. In this case, a desired recurrent parent is first crossed to a donor inbred (the non-recurrent parent) that carries the appropriate gene(s) for the Cry1D- and Cry1C-determined traits. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376).

Insect Resistance Management (IRM) strategies. Roush et al., for example, outlines two-toxin strategies, also called "pyramiding" or "stacking," for management of insecticidal transgenic crops. (The Royal Society. *Phil. Trans. R. Soc. Lond. B*. (1998) 353, 1777-1786).

On their website, the United States Environmental Protection Agency (epa.gov/oppbppdl/biopesticides/pips/bt_corn_refuge_2006.htm) publishes the following requirements for providing non-transgenic (i.e., non-B.t.) refuges (a section of non-Bt crops/corn) for use with transgenic crops producing a single Bt protein active against target pests.

"The specific structured requirements for corn borer-protected Bt (Cry1Ab or Cry1F) corn products are as follows:

Structured refuges: 20% non-Lepidopteran Bt corn refuge in Corn Belt;

50% non-Lepidopteran Bt refuge in Cotton Belt

Blocks

Internal (i.e., within the Bt field)

External (i.e., separate fields within ½ mile (¼ mile if possible) of the Bt field to maximize random mating)

In-field Strips

Strips must be at least 4 rows wide (preferably 6 rows) to reduce the effects of larval movement"

In addition, the National Corn Growers Association, on their website:

(ncga.com/insect-resistance-management-fact-sheet-bt-corn)

also provides similar guidance regarding the refuge requirements. For example:

"Requirements of the Corn Borer IRM:
Plant at least 20% of your corn acres to refuge hybrids
In cotton producing regions, refuge must be 50%
Must be planted within ½ mile of the refuge hybrids
Refuge can be planted as strips within the Bt field; the refuge strips must be at least 4 rows wide
Refuge may be treated with conventional pesticides only if economic thresholds are reached for target insect
Bt-based sprayable insecticides cannot be used on the refuge corn
Appropriate refuge must be planted on every farm with Bt corn"

As stated by Roush et al. (on pages 1780 and 1784 right column, for example), stacking or pyramiding of two different proteins each effective against the target pests and with little or no cross-resistance can allow for use of a smaller refuge. Roush suggests that for a successful stack, a refuge size of less than 10% refuge, can provide comparable resistance management to about 50% refuge for a single (non-pyramided) trait. For currently available pyramided Bt corn products, the U.S. Environmental Protection Agency requires significantly less (generally 5%) structured refuge of non-Bt corn be planted than for single trait products (generally 20%).

There are various ways of providing the IRM effects of a refuge, including various geometric planting patterns in the fields (as mentioned above) and in-bag seed mixtures, as discussed further by Roush et al. (supra), and U.S. Pat. No. 6,551,962.

The above percentages, or similar refuge ratios, can be used for the subject double or triple stacks or pyramids. For triple stacks with three sites of action against a single target pest, a goal would be zero refuge (or less than 5% refuge, for example). This is particularly true for commercial acreage—of over 10 acres for example.

All patents, patent applications, provisional applications, and publications referred to or cited herein are incorporated by reference in their entirety to the extent they are not inconsistent with the explicit teachings of this specification.

Unless specifically indicated or implied, the terms "a", "an", and "the" signify "at least one" as used herein.

Following are examples that illustrate procedures for practicing the invention. These examples should not be construed as limiting. All percentages are by weight and all solvent mixture proportions are by volume unless otherwise noted. All temperatures are in degrees Celsius.

EXAMPLES

Example 1

$^{125}$I Labeling of Cry Proteins

Iodination of Cry toxins. Purified truncated Cry toxins were was iodinated using Iodo-Beads or Iodo-gen (Pierce). Briefly, two Iodo-Beads were washed twice with 500 µl of phosphate buffered saline, PBS (20 mM sodium phosphate, 0.15 M NaCl, pH 7.5), and placed into a 1.5 ml centrifuge tube behind lead shielding. To this was added 100 µl of PBS. In a hood and through the use of proper radioactive handling techniques, 0.5 mCi Na$^{125}$I (17.4 Ci/mg, Lot 0114, Amersham) was added to the PBS solution with the Iodo-Bead. The components were allowed to react for 5 minutes at room temperature, then 2-25 ng of highly pure truncated Cry protein was added to the solution and allowed to react for an additional 3-5 minutes. The reaction was terminated by removing the solution from the iodo-beads and applying it to a 0.5 ml desalting Zeba spin column (InVitrogen) equilibrated in PBS. The iodo-bead was washed twice with 10 µl of PBS each and the wash solution also applied to the desalting column. The radioactive solution was eluted through the desalting column by centrifugation at 1,000×g for 2 min. In the case of Cry1Da, the Iodo-gen method was used to conduct the radiolabeling procedure. Using this procedure, the cry toxin in 100 mM phosphate buffer (pH 8) was first cleaned of lipopolysaccharides (LPS) by passing it through a small 0.5 ml polymyxin column multiple times. To the iodo-gen tube (Pierce Chem. Co.) was added 20 ng of the LPS-free Cry1Da toxin, then 0.5 mCi of Na$^{125}$I. The reaction mixture was shaken for 15 min at 25° C. The solution was removed from the tube, and 50 µl of 0.2M non-radiolabeled NaI added to quench the reaction. The protein was dialyzed vs PBS with 3 changes of buffer to remove any unbound $^{125}$I.

Radio-purity of the iodinated Cry proteins was determined by SDS-PAGE, phosphorimaging and gamma counting. Briefly, 2 µl of the radioactive protein was separated by SDS-PAGE. After separation, the gels were dried using a BioRad gel drying apparatus following the manufacturer's instructions. The dried gels were imaged by wrapping them in Mylar film (12 µm thick), and exposing them under a Molecular Dynamics storage phosphor screen (35 cm×43 cm), for 1 hour. The plates were developed using a Molecular Dynamics Storm 820 phosphorimager and the imaged analyzed using ImageQuant™ software. The radioactive band along with areas immediately above and below the band were cut from the gel using a razor blade and counted in a gamma counter. Radioactivity was only detected in the Cry protein band and in areas below the band. No radioactivity was detected above the band, indicating that all radioactive contaminants consisted of smaller protein components than the truncated Cry protein. These components most probably represent degradation products.

Example 2

BBMV Preparation Protocol

Preparation and Fractionation of Solubilized BBMV's. Last instar *Spodoptera frugiperda, Ostrinia nubilalis*, or *Heleothis. zea* larvae were fasted overnight and then dissected in the morning after chilling on ice for 15 minutes. The midgut tissue was removed from the body cavity, leaving behind the hindgut attached to the integument. The midgut was placed in 9× volume of ice cold homogenization buffer (300 mM mannitol, 5 mM EGTA, 17 mM tris. base, pH 7.5), supplemented with Protease Inhibitor Cocktail[1] (Sigma P-2714) diluted as recommended by the supplier. The tissue was homogenized with 15 strokes of a glass tissue homogenizer. BBMV's were prepared by the MgCl$_2$ precipitation method of Wolfersberger (1993). Briefly, an equal volume of a 24 mM MgCl$_2$ solution in 300 mM mannitol was mixed with the midgut homogenate, stirred for 5 minutes and allowed to stand on ice for 15 min. The solution was centrifuged at 2,500×g for 15 min at 4° C. The supernatant was saved and the pellet suspended into the original volume of 0.5-X diluted homogenization buffer and centrifuged again. The two supernatants were combined, centrifuged at 27,000×g for 30 min at 4° C. to form the BBMV fraction. The pellet was suspended into 10 ml homogienization buffer and supplemented to protease inhibitiors and centrifuged again at 27,000×g of r30 min at 4° C. to wash the BBMV's. The resulting pellet was suspended into BBMV Storage Buffer (10 mM HEPES, 130 mM KCl, 10% glycerol, pH 7.4) to a concentration of about 3 mg/ml protein. Protein concentration was determined by using the Bradford method (1976) with bovine serum albumin (BSA) as the standard. Alkaline phosphatase determination was made prior to freezing the samples using the Sigma assay following manufacturer's instructions. The specific activity of this marker enzyme in the BBMV fraction typically increased 7-fold compared to that found in the midgut homogenate fraction. The BBMV's were aliquoted into 250 µl samples, flash frozen in liquid $N_2$ and stored at −80° C.

[1] Final concentration of cocktail components (in µM) are AEBSF (500), EDTA (250 mM), Bestatin (32), E-64 (0.35), Leupeptin (0.25), and Aprotinin (0.075).

Example 3

Method to Measure Binding of $^{125}$I Cry Proteins to BBMV Proteins

Binding of $^{125}$I Cry Proteins to BBMV's. To determine the optimal amount of BBMV protein to use in the binding assays, a saturation curve was generated. $^{125}$I radiolabeled Cry protein (0.5 nM) was incubated for 1 hr. at 28° C. with various amounts of BBMV protein, ranging from 0-500 µg/ml in binding buffer (8 mM $NaHPO_4$, 2 mM $KH_2PO_4$, 150 mM NaCl, 0.1% bovine serum albumin, pH 7.4). Total volume was 0.5 ml. Bound $^{125}$I Cry protein was separated from unbound by sampling 150 µl of the reaction mixture in triplicate from a 1.5 ml centrifuge tube into a 500 µl centrifuge tube and centrifuging the samples at 14,000×g for 6 minutes at room temperature. The supernatant was gently removed, and the pellet gently washed three times with ice cold binding buffer. The bottom of the centrifuge containing the pellet was cut out and placed into a 13×75-mm glass culture tube. The samples were counted for 5 minutes each in the gamma counter. The counts contained in the sample were subtracted from background counts (reaction with out any protein) and was plotted versus BBMV protein concentration. The optimal amount of protein to use was determined to be 0.15 mg/ml of BBMV protein.

To determine the binding kinetics, a saturation curve was generated. Briefly, BBMV's (150 µg/ml) were incubated for 1 hr. at 28° C. with increasing concentrations of $^{125}$I Cry toxin, ranging from 0.01 to 10 nM. Total binding was determined by sampling 150 µl of each concentration in triplicate, centrifugation of the sample and counting as described above. Non-specific binding was determined in the same manner, with the addition of 1,000 nM of the homologous trypsinized non-radioactive Cry toxin added to the reaction mixture to saturate all non-specific receptor binding sites. Specific binding was calculated as the difference between total binding and non-specific binding.

Homologous and heterologous competition binding assays were conducted using 150 n/ml BBMV protein and 0.5 nM of the $^{125}$I radiolabeled Cry protein. The concentration of the competitive non-radioactive Cry toxin added to the reaction mixture ranged from 0.045 to 1,000 nM and were added at the same time as the radioactive ligand, to assure true binding competition. Incubations were carried out for 1 hr. at 28° C. and the amount of $^{125}$I Cry protein bound to its receptor toxin measured as described above with non-specific binding subtracted. One hundred percent total binding was determined in the absence of any competitor ligand. Results were plotted on a semi-logarithmic plot as percent total specific binding versus concentration of competitive ligand added.

Example 4

Summary of Results

FIG. 1 shows percent specific binding of $^{125}$I Cry1Da (0.5 nM) in BBMV's from FAW versus competition by unlabeled homologous Cry1Da (○) and heterologous Cry1Ca (■). The displacement curve for homologous competition by Cry1Da results in a sigmoidal shaped curve showing 50% displacement of the radioligand at about 1.5 nM of Cry1Da. Cry1Ca does not displace the specific binding of $^{125}$I Cry1Da at any concentration tested, up to 1,000 nM, or 2,000 times the concentration of $^{125}$I Cry1Da used in the assay.

REFERENCE LIST

Heckel, D. G., Gahan, L. J., Baxter, S. W., Zhao, J. Z., Shelton, A. M., Gould, F., and Tabashnik, B. E. (2007). The diversity of Bt resistance genes in species of Lepidoptera. J Invertebr Pathol 95, 192-197.

Luo, K., Banks, D., and Adang, M. J. (1999). Toxicity, binding, and permeability analyses of four *bacillus thuringiensis* cry1 delta-endotoxins using brush border membrane vesicles of *spodoptera exigua* and *spodoptera frugiperda*. Appl. Environ. Microbiol. 65, 457-464.

Palmer, M., Buchkremer, M, Valeva, A, and Bhakdi, S. Cysteine-specific radioiodination of proteins with fluorescein maleimide. Analytical Biochemistry 253, 175-179. 1997. Ref Type: Journal (Full)

Sambrook, J. and Russell, D. W. (2001). Molecular Cloning: A Laboratory Manual. Cold Spring Harbor Laboratory).

Schlenz, M. L., Babcock, J. M., and Storer, N. P. Response of Cry1F-resistant and Susceptible European Corn Borer and Fall Armyworm Colonies to Cry1A.105 and Cry12Ab2. DAI 0830, 2008. Indianapolis, Dow AgroSciences. Derbi Report.

Sheets, J. J. and Storer, N. P. Analysis of Cry1Ac Binding to Proteins in Brush Border Membrane Vesicles of Corn Earworm Larvae (Heleothis zea). Interactions with Cry1F Proteins and Its Implication for Resistance in the Field. DAI-0417, 1-26. 2001. Indianapolis, Dow AgroSciences.

Tabashnik, B. E., Liu, Y. B., Finson, N., Masson, L., and Heckel, D. G. (1997). One gene in diamondback moth confers resistance to four *Bacillus thuringiensis* toxins. Proc. Natl. Acad. Sci. U.S. A 94, 1640-1644.

Tabashnik, B. E., Malvar, T., Liu, Y. B., Finson, N., Borthakur, D., Shin, B. S., Park, S. H., Masson, L., de Maagd, R. A., and Bosch, D. (1996). Cross-resistance of the diamondback moth indicates altered interactions with domain II of *Bacillus thuringiensis* toxins. Appl. Environ. Microbiol. 62, 2839-2844.

Tabashnik, B. E., Roush, R. T., Earle, E. D., and Shelton, A. M. (2000). Resistance to Bt toxins. Science 287, 42.

Wolfersberger, M. G. (1993). Preparation and partial characterization of amino acid transporting brush border membrane vesicles from the larval midgut of the gypsy moth (*Lymantria dispar*). Arch. Insect Biochem. Physiol 24, 139-147.

Xu, X., Yu, L., and Wu, Y. (2005). Disruption of a cadherin gene associated with resistance to Cry1Ac {delta}-endotoxin of *Bacillus thuringiensis* in *Helicoverpa armigera*. Appl Environ Microbiol 71, 948-954.

APPENDIX A

List of delta-endotoxins—from Crickmore et al. website (cited in application)
Accession Number is to NCBI entry

| Name | Acc No. | Authors | Year | Source Strain | Comment |
| --- | --- | --- | --- | --- | --- |
| Cry1Aa1 | AAA22353 | Schnepf et al | 1985 | Bt kurstaki HD1 | |
| Cry1Aa2 | AAA22552 | Shibano et al | 1985 | Bt sotto | |
| Cry1Aa3 | BAA00257 | Shimizu et al | 1988 | Bt aizawai IPL7 | |
| Cry1Aa4 | CAA31886 | Masson et al | 1989 | Bt entomocidus | |
| Cry1Aa5 | BAA04468 | Udayasuriyan et al | 1994 | Bt Fu-2-7 | |
| Cry1Aa6 | AAA86265 | Masson et al | 1994 | Bt kurstaki NRD-12 | |
| Cry1Aa7 | AAD46139 | Osman et al | 1999 | Bt C12 | |
| Cry1Aa8 | I26149 | Liu | 1996 | | DNA sequence only |
| Cry1Aa9 | BAA77213 | Nagamatsu et al | 1999 | Bt dendrolimus T84A1 | |
| Cry1Aa10 | AAD55382 | Hou and Chen | 1999 | Bt kurstaki HD-1-02 | |
| Cry1Aa11 | CAA70856 | Tounsi et al | 1999 | Bt kurstaki | |
| Cry1Aa12 | AAP80146 | Yao et al | 2001 | Bt Ly30 | |
| Cry1Aa13 | AAM44305 | Zhong et al | 2002 | Bt sotto | |
| Cry1Aa14 | AAP40639 | Ren et al | 2002 | unpublished | |
| Cry1Aa15 | AAY66993 | Sauka et al | 2005 | Bt INTA Mol-12 | |
| Cry1Ab1 | AAA22330 | Wabiko et al | 1986 | Bt berliner 1715 | |
| Cry1Ab2 | AAA22613 | Thorne et al | 1986 | Bt kurstaki | |
| Cry1Ab3 | AAA22561 | Geiser et al | 1986 | Bt kurstaki HD1 | |
| Cry1Ab4 | BAA00071 | Kondo et al | 1987 | Bt kurstaki HD1 | |
| Cry1Ab5 | CAA28405 | Hofte et al | 1986 | Bt berliner 1715 | |
| Cry1Ab6 | AAA22420 | Hefford et al | 1987 | Bt kurstaki NRD-12 | |
| Cry1Ab7 | CAA31620 | Haider & Ellar | 1988 | Bt aizawai IC1 | |
| Cry1Ab8 | AAA22551 | Oeda et al | 1987 | Bt aizawai IPL7 | |
| Cry1Ab9 | CAA38701 | Chak & Jen | 1993 | Bt aizawai HD133 | |
| Cry1Ab10 | A29125 | Fischhoff et al | 1987 | Bt kurstaki HD1 | |
| Cry1Ab11 | I12419 | Ely & Tippett | 1995 | Bt A20 | DNA sequence only |
| Cry1Ab12 | AAC64003 | Silva-Werneck et al | 1998 | Bt kurstaki S93 | |
| Cry1Ab13 | AAN76494 | Tan et al | 2002 | Bt c005 | |
| Cry1Ab14 | AAG16877 | Meza-Basso & Theoduloz | 2000 | Native Chilean Bt | |
| Cry1Ab15 | AAO13302 | Li et al | 2001 | Bt B-Hm-16 | |
| Cry1Ab16 | AAK55546 | Yu et al | 2002 | Bt AC-11 | |
| Cry1Ab17 | AAT46415 | Huang et al | 2004 | Bt WB9 | |
| Cry1Ab18 | AAQ88259 | Stobdan et al | 2004 | Bt | |
| Cry1Ab19 | AAW31761 | Zhong et al | 2005 | Bt X-2 | |
| Cry1Ab20 | ABB72460 | Liu et al | 2006 | BtC008 | |
| Cry1Ab21 | ABS18384 | Swiecicka et al | 2007 | Bt IS5056 | |
| Cry1Ab22 | ABW87320 | Wu and Feng | 2008 | BtS2491Ab | |
| Cry1Ab-like | AAK14336 | Nagarathinam et al | 2001 | Bt kunthala RX24 | uncertain sequence |
| Cry1Ab-like | AAK14337 | Nagarathinam et al | 2001 | Bt kunthala RX28 | uncertain sequence |
| Cry1Ab-like | AAK14338 | Nagarathinam et al | 2001 | Bt kunthala RX27 | uncertain sequence |
| Cry1Ab-like | ABG88858 | Lin et al | 2006 | Bt ly4a3 | insufficient sequence |
| Cry1Ac1 | AAA22331 | Adang et al | 1985 | Bt kurstaki HD73 | |
| Cry1Ac2 | AAA22338 | Von Tersch et al | 1991 | Bt kenyae | |
| Cry1Ac3 | CAA38098 | Dardenne et al | 1990 | Bt BTS89A | |
| Cry1Ac4 | AAA73077 | Feitelson | 1991 | Bt kurstaki PS85A1 | |
| Cry1Ac5 | AAA22339 | Feitelson | 1992 | Bt kurstaki PS81GG | |
| Cry1Ac6 | AAA86266 | Masson et al | 1994 | Bt kurstaki NRD-12 | |
| Cry1Ac7 | AAB46989 | Herrera et al | 1994 | Bt kurstaki HD73 | |
| Cry1Ac8 | AAC44841 | Omolo et al | 1997 | Bt kurstaki HD73 | |
| Cry1Ac9 | AAB49768 | Gleave et al | 1992 | Bt DSIR732 | |
| Cry1Ac10 | CAA05505 | Sun | 1997 | Bt kurstaki YBT-1520 | |
| Cry1Ac11 | CAA10270 | Makhdoom & Riazuddin | 1998 | | |
| Cry1Ac12 | I12418 | Ely & Tippett | 1995 | Bt A20 | DNA sequence only |
| Cry1Ac13 | AAD38701 | Qiao et al | 1999 | Bt kurstaki HD1 | |
| Cry1Ac14 | AAQ06607 | Yao et al | 2002 | Bt Ly30 | |
| Cry1Ac15 | AAN07788 | Tzeng et al | 2001 | Bt from Taiwan | |
| Cry1Ac16 | AAU87037 | Zhao et al | 2005 | Bt H3 | |
| Cry1Ac17 | AAX18704 | Hire et al | 2005 | Bt kenyae HD549 | |
| Cry1Ac18 | AAY88347 | Kaur & Allam | 2005 | Bt SK-729 | |
| Cry1Ac19 | ABD37053 | Gao et al | 2005 | Bt C-33 | |
| Cry1Ac20 | ABB89046 | Tan et al | 2005 | | |
| Cry1Ac21 | AAY66992 | Sauka et al | 2005 | INTA Mol-12 | |
| Cry1Ac22 | ABZ01836 | Zhang & Fang | 2008 | Bt W015-1 | |
| Cry1Ac23 | CAQ30431 | Kashyap et al | 2008 | Bt | |
| Cry1Ac24 | ABL01535 | Arango et al | 2008 | Bt 146-158-01 | |
| Cry1Ac25 | FJ513324 | Guan Peng et al | 2008 | Bt Tm37-6 | No NCBI link July 2009 |
| Cry1Ac26 | FJ617446 | Guan Peng et al | 2009 | Bt Tm41-4 | No NCBI link July 2009 |
| Cry1Ac27 | FJ617447 | Guan Peng et al | 2009 | Bt Tm44-1B | No NCBI link July 2009 |
| Cry1Ac28 | ACM90319 | Li et al | 2009 | Bt Q-12 | |
| Cry1Ad1 | AAA22340 | Feitelson | 1993 | Bt aizawai PS81I | |
| Cry1Ad2 | CAA01880 | Anonymous | 1995 | Bt PS81RR1 | |
| Cry1Ae1 | AAA22410 | Lee & Aronson | 1991 | Bt alesti | |
| Cry1Af1 | AAB82749 | Kang et al | 1997 | Bt NT0423 | |
| Cry1Ag1 | AAD46137 | Mustafa | 1999 | | |
| Cry1Ah1 | AAQ14326 | Tan et al | 2000 | | |

APPENDIX A-continued

List of delta-endotoxins—from Crickmore et al. website (cited in application)
Accession Number is to NCBI entry

| | | | | | |
|---|---|---|---|---|---|
| Cry1Ah2 | ABB76664 | Qi et al | 2005 | Bt alesti | |
| Cry1Ai1 | AAO39719 | Wang et al | 2002 | | |
| Cry1A-like | AAK14339 | Nagarathinam et al | 2001 | Bt kunthala nags3 | uncertain sequence |
| Cry1Ba1 | CAA29898 | Brizzard & Whiteley | 1988 | Bt thuringiensis HD2 | |
| Cry1Ba2 | CAA65003 | Soetaert | 1996 | Bt entomocidus HD110 | |
| Cry1Ba3 | AAK63251 | Zhang et al | 2001 | | |
| Cry1Ba4 | AAK51084 | Nathan et al | 2001 | Bt entomocidus HD9 | |
| Cry1Ba5 | ABO20894 | Song et al | 2007 | Bt sfw-12 | |
| Cry1Ba6 | ABL60921 | Martins et al | 2006 | Bt S601 | |
| Cry1Bb1 | AAA22344 | Donovan et al | 1994 | Bt EG5847 | |
| Cry1Bc1 | CAA86568 | Bishop et al | 1994 | Bt morrisoni | |
| Cry1Bd1 | AAD10292 | Kuo et al | 2000 | Bt wuhanensis HD525 | |
| Cry1Bd2 | AAM93496 | Isakova et al | 2002 | Bt 834 | |
| Cry1Be1 | AAC32850 | Payne et al | 1998 | Bt PS158C2 | |
| Cry1Be2 | AAQ52387 | Baum et al | 2003 | | |
| Cry1Be3 | FJ716102 | Xiaodong Sun et al | 2009 | Bt | No NCBI link July 2009 |
| Cry1Bf1 | CAC50778 | Arnaut et al | 2001 | | |
| Cry1Bf2 | AAQ52380 | Baum et al | 2003 | | |
| Cry1Bg1 | AAO39720 | Wang et al | 2002 | | |
| Cry1Ca1 | CAA30396 | Honee et al | 1988 | Bt entomocidus 60.5 | |
| Cry1Ca2 | CAA31951 | Sanchis et al | 1989 | Bt aizawai 7.29 | |
| Cry1Ca3 | AAA22343 | Feitelson | 1993 | Bt aizawai PS81I | |
| Cry1Ca4 | CAA01886 | Van Mellaert et al | 1990 | Bt entomocidus HD110 | |
| Cry1Ca5 | CAA65457 | Strizhov | 1996 | Bt aizawai 7.29 | |
| Cry1Ca6 | AAF37224 | Yu et al | 2000 | Bt AF-2 | |
| Cry1Ca7 | AAG50438 | Aixing et al | 2000 | Bt J8 | |
| Cry1Ca8 | AAM00264 | Chen et al | 2001 | Bt c002 | |
| Cry1Ca9 | AAL79362 | Kao et al | 2003 | Bt G10-01A | |
| Cry1Ca10 | AAN16462 | Lin et al | 2003 | Bt E05-20a | |
| Cry1Ca11 | AAX53094 | Cai et al | 2005 | Bt C-33 | |
| Cry1Cb1 | M97880 | Kalman et al | 1993 | Bt galleriae HD29 | DNA sequence only |
| Cry1Cb2 | AAG35409 | Song et al | 2000 | Bt c001 | |
| Cry1Cb3 | ACD50894 | Huang et al | 2008 | Bt 087 | |
| Cry1Cb-like | AAX63901 | Thammasittirong et al | 2005 | Bt TA476-1 | insufficient sequence |
| Cry1Da1 | CAA38099 | Hofte et al | 1990 | Bt aizawai HD68 | |
| Cry1Da2 | I76415 | Payne & Sick | 1997 | | DNA sequence only |
| Cry1Db1 | CAA80234 | Lambert | 1993 | Bt BTS00349A | |
| Cry1Db2 | AAK48937 | Li et al | 2001 | Bt B-Pr-88 | |
| Cry1Dc1 | ABK35074 | Lertwiriyawong et al | 2006 | Bt JC291 | |
| Cry1Ea1 | CAA37933 | Visser et al | 1990 | Bt kenyae 4F1 | |
| Cry1Ea2 | CAA39609 | Bosse et al | 1990 | Bt kenyae | |
| Cry1Ea3 | AAA22345 | Feitelson | 1991 | Bt kenyae PS81F | |
| Cry1Ea4 | AAD04732 | Barboza-Corona et al | 1998 | Bt kenyae LBIT-147 | |
| Cry1Ea5 | A15535 | Botterman et al | 1994 | | DNA sequence only |
| Cry1Ea6 | AAL50330 | Sun et al | 1999 | Bt YBT-032 | |
| Cry1Ea7 | AAW72936 | Huehne et al | 2005 | Bt JC190 | |
| Cry1Ea8 | ABX11258 | Huang et al | 2007 | Bt HZM2 | |
| Cry1Eb1 | AAA22346 | Feitelson | 1993 | Bt aizawai PS81A2 | |
| Cry1Fa1 | AAA22348 | Chambers et al | 1991 | Bt aizawai EG6346 | |
| Cry1Fa2 | AAA22347 | Feitelson | 1993 | Bt aizawai PS81I | |
| Cry1Fb1 | CAA80235 | Lambert | 1993 | Bt BTS00349A | |
| Cry1Fb2 | BAA25298 | Masuda & Asano | 1998 | Bt morrisoni INA67 | |
| Cry1Fb3 | AAF21767 | Song et al | 1998 | Bt morrisoni | |
| Cry1Fb4 | AAC10641 | Payne et al | 1997 | | |
| Cry1Fb5 | AAO13295 | Li et al | 2001 | Bt B-Pr-88 | |
| Cry1Fb6 | ACD50892 | Huang et al | 2008 | Bt 012 | |
| Cry1Fb7 | ACD50893 | Huang et al | 2008 | Bt 087 | |
| Cry1Ga1 | CAA80233 | Lambert | 1993 | Bt BTS0349A | |
| Cry1Ga2 | CAA70506 | Shevelev et al | 1997 | Bt wuhanensis | |
| Cry1Gb1 | AAD10291 | Kuo & Chak | 1999 | Bt wuhanensis HD525 | |
| Cry1Gb2 | AAO13756 | Li et al | 2000 | Bt B-Pr-88 | |
| Cry1Gc | AAQ52381 | Baum et al | 2003 | | |
| Cry1Ha1 | CAA80236 | Lambert | 1993 | Bt BTS02069AA | |
| Cry1Hb1 | AAA79694 | Koo et al | 1995 | Bt morrisoni BF190 | |
| Cry1H-like | AAF01213 | Srifah et al | 1999 | Bt JC291 | insufficient sequence |
| Cry1Ia1 | CAA44633 | Tailor et al | 1992 | Bt kurstaki | |
| Cry1Ia2 | AAA22354 | Gleave et al | 1993 | Bt kurstaki | |
| Cry1Ia3 | AAC36999 | Shin et al | 1995 | Bt kurstaki HD1 | |
| Cry1Ia4 | AAB00958 | Kostichka et al | 1996 | Bt AB88 | |
| Cry1Ia5 | CAA70124 | Selvapandiyan | 1996 | Bt 61 | |
| Cry1Ia6 | AAC26910 | Zhong et al | 1998 | Bt kurstaki S101 | |
| Cry1Ia7 | AAM73516 | Porcar et al | 2000 | Bt | |
| Cry1Ia8 | AAK66742 | Song et al | 2001 | | |
| Cry1Ia9 | AAQ08616 | Yao et al | 2002 | Bt Ly30 | |
| Cry1Ia10 | AAP86782 | Espindola et al | 2003 | Bt thuringiensis | |
| Cry1Ia11 | CAC85964 | Tounsi et al | 2003 | Bt kurstaki BNS3 | |
| Cry1Ia12 | AAV53390 | Grossi de Sa et al | 2005 | Bt | |

APPENDIX A-continued

List of delta-endotoxins—from Crickmore et al. website (cited in application)
Accession Number is to NCBI entry

| | | | | | |
|---|---|---|---|---|---|
| Cry1Ia13 | ABF83202 | Martins et al | 2006 | Bt | |
| Cry1Ia14 | ACG63871 | Liu & Guo | 2008 | Bt11 | |
| Cry1Ia15 | FJ617445 | Guan Peng et al | 2009 | Bt E-1B | No NCBI link July 2009 |
| Cry1Ia16 | FJ617448 | Guan Peng et al | 2009 | Bt E-1A | No NCBI link July 2009 |
| Cry1Ib1 | AAA82114 | Shin et al | 1995 | Bt entomocidus BP465 | |
| Cry1Ib2 | ABW88019 | Guan et al | 2007 | Bt PP61 | |
| Cry1Ib3 | ACD75515 | Liu & Guo | 2008 | Bt GS8 | |
| Cry1Ic1 | AAC62933 | Osman et al | 1998 | Bt C18 | |
| Cry1Ic2 | AAE71691 | Osman et al | 2001 | | |
| Cry1Id1 | AAD44366 | Choi | 2000 | | |
| Cry1Ie1 | AAG43526 | Song et al | 2000 | Bt BTC007 | |
| Cry1If1 | AAQ52382 | Baum et al | 2003 | | |
| Cry1I-like | AAC31094 | Payne et al | 1998 | | insufficient sequence |
| Cry1I-like | ABG88859 | Lin & Fang | 2006 | Bt ly4a3 | insufficient sequence |
| Cry1Ja1 | AAA22341 | Donovan | 1994 | Bt EG5847 | |
| Cry1Jb1 | AAA98959 | Von Tersch & Gonzalez | 1994 | Bt EG5092 | |
| Cry1Jc1 | AAC31092 | Payne et al | 1998 | | |
| Cry1Jc2 | AAQ52372 | Baum et al | 2003 | | |
| Cry1Jd1 | CAC50779 | Arnaut et al | 2001 | Bt | |
| Cry1Ka1 | AAB00376 | Koo et al | 1995 | Bt morrisoni BF190 | |
| Cry1La1 | AAS60191 | Je et al | 2004 | Bt kurstaki K1 | |
| Cry1-like | AAC31091 | Payne et al | 1998 | | insufficient sequence |
| Cry2Aa1 | AAA22335 | Donovan et al | 1989 | Bt kurstaki | |
| Cry2Aa2 | AAA83516 | Widner & Whiteley | 1989 | Bt kurstaki HD1 | |
| Cry2Aa3 | D86064 | Sasaki et al | 1997 | Bt sotto | DNA sequence only |
| Cry2Aa4 | AAC04867 | Misra et al | 1998 | Bt kenyae HD549 | |
| Cry2Aa5 | CAA10671 | Yu & Pang | 1999 | Bt SL39 | |
| Cry2Aa6 | CAA10672 | Yu & Pang | 1999 | Bt YZ71 | |
| Cry2Aa7 | CAA10670 | Yu & Pang | 1999 | Bt CY29 | |
| Cry2Aa8 | AAO13734 | Wei et al | 2000 | Bt Dongbei 66 | |
| Cry2Aa9 | AAO13750 | Zhang et al | 2000 | | |
| Cry2Aa10 | AAQ04263 | Yao et al | 2001 | | |
| Cry2Aa11 | AAQ52384 | Baum et al | 2003 | | |
| Cry2Aa12 | ABI83671 | Tan et al | 2006 | Bt Rpp39 | |
| Cry2Aa13 | ABL01536 | Arango et al | 2008 | Bt 146-158-01 | |
| Cry2Aa14 | ACF04939 | Hire et al | 2008 | Bt HD-550 | |
| Cry2Ab1 | AAA22342 | Widner & Whiteley | 1989 | Bt kurstaki HD1 | |
| Cry2Ab2 | CAA39075 | Dankocsik et al | 1990 | Bt kurstaki HD1 | |
| Cry2Ab3 | AAG36762 | Chen et al | 1999 | Bt BTC002 | |
| Cry2Ab4 | AAO13296 | Li et al | 2001 | Bt B-Pr-88 | |
| Cry2Ab5 | AAQ04609 | Yao et al | 2001 | Bt ly30 | |
| Cry2Ab6 | AAP59457 | Wang et al | 2003 | Bt WZ-7 | |
| Cry2Ab7 | AAZ66347 | Udayasuriyan et al | 2005 | Bt 14-1 | |
| Cry2Ab8 | ABC95996 | Huang et al | 2006 | Bt WB2 | |
| Cry2Ab9 | ABC74968 | Zhang et al | 2005 | Bt LLB6 | |
| Cry2Ab10 | EF157306 | Lin et al | 2006 | Bt LyD | |
| Cry2Ab11 | CAM84575 | Saleem et al | 2007 | Bt CMBL-BT1 | |
| Cry2Ab12 | ABM21764 | Lin et al | 2007 | Bt LyD | |
| Cry2Ab13 | ACG76120 | Zhu et al | 2008 | Bt ywc5-4 | |
| Cry2Ab14 | ACG76121 | Zhu et al | 2008 | Bt Bts | |
| Cry2Ac1 | CAA40536 | Aronson | 1991 | Bt shanghai S1 | |
| Cry2Ac2 | AAG35410 | Song et al | 2000 | | |
| Cry2Ac3 | AAQ52385 | Baum et al | 2003 | | |
| Cry2Ac4 | ABC95997 | Huang et al | 2006 | Bt WB9 | |
| Cry2Ac5 | ABC74969 | Zhang et al | 2005 | | |
| Cry2Ac6 | ABC74793 | Xia et al | 2006 | Bt wuhanensis | |
| Cry2Ac7 | CAL18690 | Saleem et al | 2008 | Bt SBSBT-1 | |
| Cry2Ac8 | CAM09325 | Saleem et al | 2007 | Bt CMBL-BT1 | |
| Cry2Ac9 | CAM09326 | Saleem et al | 2007 | Bt CMBL-BT2 | |
| Cry2Ac10 | ABN15104 | Bai et al | 2007 | Bt QCL-1 | |
| Cry2Ac11 | CAM83895 | Saleem et al | 2007 | Bt HD29 | |
| Cry2Ac12 | CAM83896 | Saleem et al | 2007 | Bt CMBL-BT3 | |
| Cry2Ad1 | AAF09583 | Choi et al | 1999 | Bt BR30 | |
| Cry2Ad2 | ABC86927 | Huang et al | 2006 | Bt WB10 | |
| Cry2Ad3 | CAK29504 | Saleem et al | 2006 | Bt 5_2AcT(1) | |
| Cry2Ad4 | CAM32331 | Saleem et al | 2007 | Bt CMBL-BT2 | |
| Cry2Ad5 | CAO78739 | Saleem et al | 2007 | Bt HD29 | |
| Cry2Ae1 | AAQ52362 | Baum et al | 2003 | | |
| Cry2Af1 | ABO30519 | Beard et al | 2007 | Bt C81 | |
| Cry2Ag | ACH91610 | Zhu et al | 2008 | Bt JF19-2 | |
| Cry2Ah | EU939453 | Zhang et al | 2008 | Bt | No NCBI link July 2009 |
| Cry2Ah2 | ACL80665 | Zhang et al | 2009 | Bt BRC-ZQL3 | |
| Cry2Ai | FJ788388 | Udayasuriyan et al | 2009 | Bt | No NCBI link July 2009 |
| Cry3Aa1 | AAA22336 | Herrnstadt et al | 1987 | Bt san diego | |
| Cry3Aa2 | AAA22541 | Sekar et al | 1987 | Bt tenebrionis | |
| Cry3Aa3 | CAA68482 | Hofte et al | 1987 | | |
| Cry3Aa4 | AAA22542 | McPherson et al | 1988 | Bt tenebrionis | |

APPENDIX A-continued

List of delta-endotoxins—from Crickmore et al. website (cited in application)
Accession Number is to NCBI entry

| Name | Accession | Authors | Year | Strain | Notes |
|---|---|---|---|---|---|
| Cry3Aa5 | AAA50255 | Donovan et al | 1988 | Bt morrisoni EG2158 | |
| Cry3Aa6 | AAC43266 | Adams et al | 1994 | Bt tenebrionis | |
| Cry3Aa7 | CAB41411 | Zhang et al | 1999 | Bt 22 | |
| Cry3Aa8 | AAS79487 | Gao and Cai | 2004 | Bt YM-03 | |
| Cry3Aa9 | AAW05659 | Bulla and Candas | 2004 | Bt UTD-001 | |
| Cry3Aa10 | AAU29411 | Chen et al | 2004 | Bt 886 | |
| Cry3Aa11 | AAW82872 | Kurt et al | 2005 | Bt tenebrionis Mm2 | |
| Cry3Aa12 | ABY49136 | Sezen et al | 2008 | Bt tenebrionis | |
| Cry3Ba1 | CAA34983 | Sick et al | 1990 | Bt tolworthi 43F | |
| Cry3Ba2 | CAA00645 | Peferoen et al | 1990 | Bt PGSI208 | |
| Cry3Bb1 | AAA22334 | Donovan et al | 1992 | Bt EG4961 | |
| Cry3Bb2 | AAA74198 | Donovan et al | 1995 | Bt EG5144 | |
| Cry3Bb3 | I15475 | Peferoen et al | 1995 | | DNA sequence only |
| Cry3Ca1 | CAA42469 | Lambert et al | 1992 | Bt kurstaki BtI109P | |
| Cry4Aa1 | CAA68485 | Ward & Ellar | 1987 | Bt israelensis | |
| Cry4Aa2 | BAA00179 | Sen et al | 1988 | Bt israelensis HD522 | |
| Cry4Aa3 | CAD30148 | Berry et al | 2002 | Bt israelensis | |
| Cry4A-like | AAY96321 | Mahalakshmi et al | 2005 | Bt LDC-9 | insufficient sequence |
| Cry4Ba1 | CAA30312 | Chungjatpornchai et al | 1988 | Bt israelensis 4Q2-72 | |
| Cry4Ba2 | CAA30114 | Tungpradubkul et al | 1988 | Bt israelensis | |
| Cry4Ba3 | AAA22337 | Yamamoto et al | 1988 | Bt israelensis | |
| Cry4Ba4 | BAA00178 | Sen et al | 1988 | Bt israelensis HD522 | |
| Cry4Ba5 | CAD30095 | Berry et al | 2002 | Bt israelensis | |
| Cry4Ba-like | ABC47686 | Mahalakshmi et al | 2005 | Bt LDC-9 | insufficient sequence |
| Cry4Ca1 | EU646202 | Shu et al | 2008 | | No NCBI link July 2009 |
| Cry4Cb1 | FJ403208 | Jun & Furong | 2008 | Bt HS18-1 | No NCBI link July 2009 |
| Cry4Cb2 | FJ597622 | Jun & Furong | 2008 | BT Ywc2-8 | No NCBI link July 2009 |
| Cry4Cc1 | FJ403207 | Jun & Furong | 2008 | Bt MC28 | No NCBI link July 2009 |
| Cry5Aa1 | AAA67694 | Narva et al | 1994 | Bt darmstadiensis PS17 | |
| Cry5Ab1 | AAA67693 | Narva et al | 1991 | Bt darmstadiensis PS17 | |
| Cry5Ac1 | I34543 | Payne et al | 1997 | | DNA sequence only |
| Cry5Ad1 | ABQ82087 | Lenane et al | 2007 | Bt L366 | |
| Cry5Ba1 | AAA68598 | Foncerrada & Narva | 1997 | Bt PS86Q3 | |
| Cry5Ba2 | ABW88931 | Guo et al | 2008 | YBT 1518 | |
| Cry6Aa1 | AAA22357 | Narva et al | 1993 | Bt PS52A1 | |
| Cry6Aa2 | AAM46849 | Bai et al | 2001 | YBT 1518 | |
| Cry6Aa3 | ABH03377 | Jia et al | 2006 | Bt 96418 | |
| Cry6Ba1 | AAA22358 | Narva et al | 1991 | Bt PS69D1 | |
| Cry7Aa1 | AAA22351 | Lambert et al | 1992 | Bt galleriae PGSI245 | |
| Cry7Ab1 | AAA21120 | Narva & Fu | 1994 | Bt dakota HD511 | |
| Cry7Ab2 | AAA21121 | Narva & Fu | 1994 | Bt kumamotoensis 867 | |
| Cry7Ab3 | ABX24522 | Song et al | 2008 | Bt WZ-9 | |
| Cry7Ab4 | EU380678 | Shu et al | 2008 | Bt | No NCBI link July 2009 |
| Cry7Ab5 | ABX79555 | Aguirre-Arzola et al | 2008 | Bt monterrey GM-33 | |
| Cry7Ab6 | ACI44005 | Deng et al | 2008 | Bt HQ122 | |
| Cry7Ab7 | FJ940776 | Wang et al | 2009 | | No NCBI link September 2009 |
| Cry7Ab8 | GU145299 | Feng Jing | 2009 | | No NCBI link November 2009 |
| Cry7Ba1 | ABB70817 | Zhang et al | 2006 | Bt huazhongensis | |
| Cry7Ca1 | ABR67863 | Gao et al | 2007 | Bt BTH-13 | |
| Cry7Da1 | ACQ99547 | Yi et al | 2009 | Bt LH-2 | |
| Cry8Aa1 | AAA21117 | Narva & Fu | 1992 | Bt kumamotoensis | |
| Cry8Ab1 | EU044830 | Cheng et al | 2007 | Bt B-JJX | No NCBI link July 2009 |
| Cry8Ba1 | AAA21118 | Narva & Fu | 1993 | Bt kumamotoensis | |
| Cry8Bb1 | CAD57542 | Abad et al | 2002 | | |
| Cry8Bc1 | CAD57543 | Abad et al | 2002 | | |
| Cry8Ca1 | AAA21119 | Sato et al. | 1995 | Bt japonensis Buibui | |
| Cry8Ca2 | AAR98783 | Shu et al | 2004 | Bt HBF-1 | |
| Cry8Ca3 | EU625349 | Du et al | 2008 | Bt FTL-23 | No NCBI link July 2009 |
| Cry8Da1 | BAC07226 | Asano et al | 2002 | Bt galleriae | |
| Cry8Da2 | BD133574 | Asano et al | 2002 | Bt | DNA sequence only |
| Cry8Da3 | BD133575 | Asano et al | 2002 | Bt | DNA sequence only |
| Cry8Db1 | BAF93483 | Yamaguchi et al | 2007 | Bt BBT2-5 | |
| Cry8Ea1 | AAQ73470 | Fuping et al | 2003 | Bt 185 | |
| Cry8Ea2 | EU047597 | Liu et al | 2007 | Bt B-DLL | No NCBI link July 2009 |
| Cry8Fa1 | AAT48690 | Shu et al | 2004 | Bt 185 | also AAW81032 |
| Cry8Ga1 | AAT46073 | Shu et al | 2004 | Bt HBF-18 | |
| Cry8Ga2 | ABC42043 | Yan et al | 2008 | Bt 145 | |
| Cry8Ga3 | FJ198072 | Xiaodong et al | 2008 | Bt FCD114 | No NCBI link July 2009 |
| Cry8Ha1 | EF465532 | Fuping et al | 2006 | Bt 185 | No NCBI link July 2009 |
| Cry8Ia1 | EU381044 | Yan et al | 2008 | Bt su4 | No NCBI link July 2009 |
| Cry8Ja1 | EU625348 | Du et al | 2008 | Bt FPT-2 | No NCBI link July 2009 |
| Cry8Ka1 | FJ422558 | Quezado et al | 2008 | | No NCBI link July 2009 |
| Cry8Ka2 | ACN87262 | Noguera & Ibarra | 2009 | Bt kenyae | |
| Cry8-like | FJ770571 | Noguera & Ibarra | 2009 | Bt canadensis | DNA sequence only |
| Cry8-like | ABS53003 | Mangena et al | 2007 | Bt | |
| Cry9Aa1 | CAA41122 | Shevelev et al | 1991 | Bt galleriae | |
| Cry9Aa2 | CAA41425 | Gleave et al | 1992 | Bt DSIR517 | |

APPENDIX A-continued

List of delta-endotoxins—from Crickmore et al. website (cited in application)
Accession Number is to NCBI entry

| Name | Accession | Authors | Year | Strain | Notes |
|---|---|---|---|---|---|
| Cry9Aa3 | GQ249293 | Su et al | 2009 | Bt SC5(D2) | No NCBI link July 2009 |
| Cry9Aa4 | GQ249294 | Su et al | 2009 | Bt T03C001 | No NCBI link July 2009 |
| Cry9Aa like | AAQ52376 | Baum et al | 2003 | | incomplete sequence |
| Cry9Ba1 | CAA52927 | Shevelev et al | 1993 | Bt galleriae | |
| Cry9Bb1 | AAV28716 | Silva-Werneck et al | 2004 | Bt japonensis | |
| Cry9Ca1 | CAA85764 | Lambert et al | 1996 | Bt tolworthi | |
| Cry9Ca2 | AAQ52375 | Baum et al | 2003 | | |
| Cry9Da1 | BAA19948 | Asano | 1997 | Bt japonensis N141 | |
| Cry9Da2 | AAB97923 | Wasano & Ohba | 1998 | Bt japonensis | |
| Cry9Da3 | GQ249295 | Su et al | 2009 | Bt T03B001 | No NCBI link July 2009 |
| Cry9Da4 | GQ249297 | Su et al | 2009 | Bt T03B001 | No NCBI link July 2009 |
| Cry9Db1 | AAX78439 | Flannagan & Abad | 2005 | Bt kurstaki DP1019 | |
| Cry9Ea1 | BAA34908 | Midoh & Oyama | 1998 | Bt aizawai SSK-10 | |
| Cry9Ea2 | AAO12908 | Li et al | 2001 | Bt B-Hm-16 | |
| Cry9Ea3 | ABM21765 | Lin et al | 2006 | Bt lyA | |
| Cry9Ea4 | ACE88267 | Zhu et al | 2008 | Bt ywc5-4 | |
| Cry9Ea5 | ACF04743 | Zhu et al | 2008 | Bts | |
| Cry9Ea6 | ACG63872 | Liu & Guo | 2008 | Bt 11 | |
| Cry9Ea7 | FJ380927 | Sun et al | 2008 | | No NCBI link July 2009 |
| Cry9Ea8 | GQ249292 | Su et al | 2009 | GQ249292 | No NCBI link July 2009 |
| Cry9Eb1 | CAC50780 | Arnaut et al | 2001 | | |
| Cry9Eb2 | GQ249298 | Su et al | 2009 | Bt T03B001 | No NCBI link July 2009 |
| Cry9Ec1 | AAC63366 | Wasano et al | 2003 | Bt galleriae | |
| Cry9Ed1 | AAX78440 | Flannagan & Abad | 2005 | Bt kurstaki DP1019 | |
| Cry9Ee1 | GQ249296 | Su et al | 2009 | Bt T03B001 | No NCBI link August 2009 |
| Cry9-like | AAC63366 | Wasano et al | 1998 | Bt galleriae | insufficient sequence |
| Cry10Aa1 | AAA22614 | Thorne et al | 1986 | Bt israelensis | |
| Cry10Aa2 | E00614 | Aran & Toomasu | 1996 | Bt israelensis ONR-60A | DNA sequence only |
| Cry10Aa3 | CAD30098 | Berry et al | 2002 | Bt israelensis | |
| Cry10A-like | DQ167578 | Mahalakshmi et al | 2006 | Bt LDC-9 | incomplete sequence |
| Cry11Aa1 | AAA22352 | Donovan et al | 1988 | Bt israelensis | |
| Cry11Aa2 | AAA22611 | Adams et al | 1989 | Bt israelensis | |
| Cry11Aa3 | CAD30081 | Berry et al | 2002 | Bt israelensis | |
| Cry11Aa-like | DQ166531 | Mahalakshmi et al | 2007 | Bt LDC-9 | incomplete sequence |
| Cry11Ba1 | CAA60504 | Delecluse et al | 1995 | Bt jegathesan 367 | |
| Cry11Bb1 | AAC97162 | Orduz et al | 1998 | Bt medellin | |
| Cry12Aa1 | AAA22355 | Narva et al | 1991 | Bt PS33F2 | |
| Cry13Aa1 | AAA22356 | Narva et al | 1992 | Bt PS63B | |
| Cry14Aa1 | AAA21516 | Narva et al | 1994 | Bt sotto PS80JJ1 | |
| Cry15Aa1 | AAA22333 | Brown & Whiteley | 1992 | Bt thompsoni | |
| Cry16Aa1 | CAA63860 | Barloy et al | 1996 | Cb malaysia CH18 | |
| Cry17Aa1 | CAA67841 | Barloy et al | 1998 | Cb malaysia CH18 | |
| Cry18Aa1 | CAA67506 | Zhang et al | 1997 | Paenibacillus popilliae | |
| Cry18Ba1 | AAF89667 | Patel et al | 1999 | Paenibacillus popilliae | |
| Cry18Ca1 | AAF89668 | Patel et al | 1999 | Paenibacillus popilliae | |
| Cry19Aa1 | CAA68875 | Rosso & Delecluse | 1996 | Bt jegathesan 367 | |
| Cry19Ba1 | BAA32397 | Hwang et al | 1998 | Bt higo | |
| Cry20Aa1 | AAB93476 | Lee & Gill | 1997 | Bt fukuokaensis | |
| Cry20Ba1 | ACS93601 | Noguera & Ibarra | 2009 | Bt higo LBIT-976 | |
| Cry20-like | GQ144333 | Yi et al | 2009 | Bt Y-5 | DNA sequence only |
| Cry21Aa1 | I32932 | Payne et al | 1996 | | DNA sequence only |
| Cry21Aa2 | I66477 | Feitelson | 1997 | | DNA sequence only |
| Cry21Ba1 | BAC06484 | Sato & Asano | 2002 | Bt roskildiensis | |
| Cry22Aa1 | I34547 | Payne et al | 1997 | | DNA sequence only |
| Cry22Aa2 | CAD43579 | Isaac et al | 2002 | Bt | |
| Cry22Aa3 | ACD93211 | Du et al | 2008 | Bt FZ-4 | |
| Cry22Ab1 | AAK50456 | Baum et al | 2000 | Bt EG4140 | |
| Cry22Ab2 | CAD43577 | Isaac et al | 2002 | Bt | |
| Cry22Ba1 | CAD43578 | Isaac et al | 2002 | Bt | |
| Cry23Aa1 | AAF76375 | Donovan et al | 2000 | Bt | Binary with Cry37Aa1 |
| Cry24Aa1 | AAC61891 | Kawalek and Gill | 1998 | Bt jegathesan | |
| Cry24Ba1 | BAD32657 | Ohgushi et al | 2004 | Bt sotto | |
| Cry24Ca1 | CAJ43600 | Beron & Salerno | 2005 | Bt FCC-41 | |
| Cry25Aa1 | AAC61892 | Kawalek and Gill | 1998 | Bt jegathesan | |
| Cry26Aa1 | AAD25075 | Wojciechowska et al | 1999 | Bt finitimus B-1166 | |
| Cry27Aa1 | BAA82796 | Saitoh | 1999 | Bt higo | |
| Cry28Aa1 | AAD24189 | Wojciechowska et al | 1999 | Bt finitimus B-1161 | |
| Cry28Aa2 | AAG00235 | Moore and Debro | 2000 | Bt finitimus | |
| Cry29Aa1 | CAC80985 | Delecluse et al | 2000 | Bt medellin | |
| Cry30Aa1 | CAC80986 | Delecluse et al | 2000 | Bt medellin | |
| Cry30Ba1 | BAD00052 | Ito et al | 2003 | Bt entomocidus | |
| Cry30Ca1 | BAD67157 | Ohgushi et al | 2004 | Bt sotto | |
| Cry30Ca2 | ACU24781 | Sun and Park | 2009 | Bt jegathesan 367 | |
| Cry30Da1 | EF095955 | Shu et al | 2006 | Bt Y41 | No NCBI link July 2009 |
| Cry30Db1 | BAE80088 | Kishida et al | 2006 | Bt aizawai BUN1-14 | |
| Cry30Ea1 | ACC95445 | Fang et al | 2007 | Bt S2160-1 | |
| Cry30Ea2 | FJ499389 | Jun et al | 2008 | Bt Ywc2-8 | No NCBI link July 2009 |

APPENDIX A-continued

List of delta-endotoxins—from Crickmore et al. website (cited in application)
Accession Number is to NCBI entry

| Name | Accession | Author | Year | Strain | Notes |
|---|---|---|---|---|---|
| Cry30Fa1 | ACI22625 | Tan et al | 2008 | Bt MC28 | |
| Cry30Ga1 | ACG60020 | Zhu et al | 2008 | Bt HS18-1 | |
| Cry31Aa1 | BAB11757 | Saitoh & Mizuki | 2000 | Bt 84-HS-1-11 | |
| Cry31Aa2 | AAL87458 | Jung and Cote | 2000 | Bt M15 | |
| Cry31Aa3 | BAE79808 | Uemori et al | 2006 | Bt B0195 | |
| Cry31Aa4 | BAF32571 | Yasutake et al | 2006 | Bt 79-25 | |
| Cry31Aa5 | BAF32572 | Yasutake et al | 2006 | Bt 92-10 | |
| Cry31Ab1 | BAE79809 | Uemori et al | 2006 | Bt B0195 | |
| Cry31Ab2 | BAF32570 | Yasutake et al | 2006 | Bt 31-5 | |
| Cry31Ac1 | BAF34368 | Yasutake et al | 2006 | Bt 87-29 | |
| Cry32Aa1 | AAG36711 | Balasubramanian et al | 2001 | Bt yunnanensis | |
| Cry32Ba1 | BAB78601 | Takebe et al | 2001 | Bt | |
| Cry32Ca1 | BAB78602 | Takebe et al | 2001 | Bt | |
| Cry32Da1 | BAB78603 | Takebe et al | 2001 | Bt | |
| Cry33Aa1 | AAL26871 | Kim et al | 2001 | Bt dakota | |
| Cry34Aa1 | AAG50341 | Ellis et al | 2001 | Bt PS80JJ1 | Binary with Cry35Aa1 |
| Cry34Aa2 | AAK64560 | Rupar et al | 2001 | Bt EG5899 | Binary with Cry35Aa2 |
| Cry34Aa3 | AAT29032 | Schnepf et al | 2004 | Bt PS69Q | Binary with Cry35Aa3 |
| Cry34Aa4 | AAT29030 | Schnepf et al | 2004 | Bt PS185GG | Binary with Cry35Aa4 |
| Cry34Ab1 | AAG41671 | Moellenbeck et al | 2001 | Bt PS149B1 | Binary with Cry35Ab1 |
| Cry34Ac1 | AAG50118 | Ellis et al | 2001 | Bt PS167H2 | Binary with Cry35Ac1 |
| Cry34Ac2 | AAK64562 | Rupar et al | 2001 | Bt EG9444 | Binary with Cry35Ab2 |
| Cry34Ac3 | AAT29029 | Schnepf et al | 2004 | Bt KR1369 | Binary with Cry35Ab3 |
| Cry34Ba1 | AAK64565 | Rupar et al | 2001 | Bt EG4851 | Binary with Cry35Ba1 |
| Cry34Ba2 | AAT29033 | Schnepf et al | 2004 | Bt PS201L3 | Binary with Cry35Ba2 |
| Cry34Ba3 | AAT29031 | Schnepf et al | 2004 | Bt PS201HH2 | Binary with Cry35Ba3 |
| Cry35Aa1 | AAG50342 | Ellis et al | 2001 | Bt PS80JJ1 | Binary with Cry34Aa1 |
| Cry35Aa2 | AAK64561 | Rupar et al | 2001 | Bt EG5899 | Binary with Cry34Aa2 |
| Cry35Aa3 | AAT29028 | Schnepf et al | 2004 | Bt PS69Q | Binary with Cry34Aa3 |
| Cry35Aa4 | AAT29025 | Schnepf et al | 2004 | Bt PS185GG | Binary with Cry34Aa4 |
| Cry35Ab1 | AAG41672 | Moellenbeck et al | 2001 | Bt PS149B1 | Binary with Cry34Ab1 |
| Cry35Ab2 | AAK64563 | Rupar et al | 2001 | Bt EG9444 | Binary with Cry34Ac2 |
| Cry35Ab3 | AY536891 AAT29024 | | 2004 | Bt KR1369 | Binary with Cry34Ab3 |
| Cry35Ac1 | AAG50117 | Ellis et al | 2001 | Bt PS167H2 | Binary with Cry34Ac1 |
| Cry35Ba1 | AAK64566 | Rupar et al | 2001 | Bt EG4851 | Binary with Cry34Ba1 |
| Cry35Ba2 | AAT29027 | Schnepf et al | 2004 | Bt PS201L3 | Binary with Cry34Ba2 |
| Cry35Ba3 | AAT29026 | Schnepf et al | 2004 | Bt PS201HH2 | Binary with Cry34Ba3 |
| Cry36Aa1 | AAK64558 | Rupar et al | 2001 | Bt | |
| Cry37Aa1 | AAF76376 | Donovan et al | 2000 | Bt | Binary with Cry23Aa |
| Cry38Aa1 | AAK64559 | Rupar et al | 2000 | Bt | |
| Cry39Aa1 | BAB72016 | Ito et al | 2001 | Bt aizawai | |
| Cry40Aa1 | BAB72018 | Ito et al | 2001 | Bt aizawai | |
| Cry40Ba1 | BAC77648 | Ito et al | 2003 | Bun1-14 | |
| Cry40Ca1 | EU381045 | Shu et al | 2008 | Bt Y41 | No NCBI link July 2009 |
| Cry40Da1 | ACF15199 | Zhang et al | 2008 | Bt S2096-2 | |
| Cry41Aa1 | BAD35157 | Yamashita et al | 2003 | Bt A1462 | |
| Cry41Ab1 | BAD35163 | Yamashita et al | 2003 | Bt A1462 | |
| Cry42Aa1 | BAD35166 | Yamashita et al | 2003 | Bt A1462 | |
| Cry43Aa1 | BAD15301 | Yokoyama and Tanaka | 2003 | P. lentimorbus semadara | |
| Cry43Aa2 | BAD95474 | Nozawa | 2004 | P. popilliae popilliae | |
| Cry43Ba1 | BAD15303 | Yokoyama and Tanaka | 2003 | P. lentimorbus semadara | |
| Cry43-like | BAD15305 | Yokoyama and Tanaka | 2003 | P. lentimorbus semadara | |
| Cry44Aa | BAD08532 | Ito et al | 2004 | Bt entomocidus INA288 | |
| Cry45Aa | BAD22577 | Okumura et al | 2004 | Bt 89-T-34-22 | |
| Cry46Aa | BAC79010 | Ito et al | 2004 | Bt dakota | |
| Cry46Aa2 | BAG68906 | Ishikawa et al | 2008 | Bt A1470 | |
| Cry46Ab | BAD35170 | Yamagiwa et al | 2004 | Bt | |
| Cry47Aa | AAY24695 | Kongsuwan et al | 2005 | Bt CAA890 | |
| Cry48Aa | CAJ18351 | Jones and Berry | 2005 | Bs IAB59 | binary with 49Aa |
| Cry48Aa2 | CAJ86545 | Jones and Berry | 2006 | Bs 47-6B | binary with 49Aa2 |
| Cry48Aa3 | CAJ86546 | Jones and Berry | 2006 | Bs NHA15b | binary with 49Aa3 |
| Cry48Ab | CAJ86548 | Jones and Berry | 2006 | Bs LP1G | binary with 49Ab1 |
| Cry48Ab2 | CAJ86549 | Jones and Berry | 2006 | Bs 2173 | binary with 49Aa4 |
| Cry49Aa | CAH56541 | Jones and Berry | 2005 | Bs IAB59 | binary with 48Aa |
| Cry49Aa2 | CAJ86541 | Jones and Berry | 2006 | Bs 47-6B | binary with 48Aa2 |
| Cry49Aa3 | CAJ86543 | Jones and Berry | 2006 | BsNHA15b | binary with 48Aa3 |
| Cry49Aa4 | CAJ86544 | Jones and Berry | 2006 | Bs 2173 | binary with 48Ab2 |
| Cry49Ab1 | CAJ86542 | Jones and Berry | 2006 | Bs LP1G | binary with 48Ab1 |
| Cry50Aa1 | BAE86999 | Ohgushi et al | 2006 | Bt sotto | |
| Cry51Aa1 | ABI14444 | Meng et al | 2006 | Bt F14-1 | |
| Cry52Aa1 | EF613489 | Song et al | 2007 | Bt Y41 | No NCBI link July 2009 |
| Cry52Ba1 | FJ361760 | Jun et al | 2008 | Bt BM59-2 | No NCBI link July 2009 |
| Cry53Aa1 | EF633476 | Song et al | 2007 | Bt Y41 | No NCBI link July 2009 |
| Cry53Ab1 | FJ361759 | Jun et al | 2008 | Bt MC28 | No NCBI link July 2009 |
| Cry54Aa1 | ACA52194 | Tan et al | 2009 | Bt MC28 | |
| Cry55Aa1 | ABW88932 | Guo et al | 2008 | YBT 1518 | |
| Cry55Aa2 | AAE33526 | Bradfisch et al | 2000 | BT Y41 | |

APPENDIX A-continued

List of delta-endotoxins—from Crickmore et al. website (cited in application)
Accession Number is to NCBI entry

| | | | | | | | |
|---|---|---|---|---|---|---|---|
| Cry56Aa1 | FJ597621 | | Jun & Furong | 2008 | Bt Ywc2-8 | No NCBI link July 2009 | |
| Cry56Aa2 | GQ483512 | | Guan Peng et al | 2009 | Bt G7-1 | No NCBI link August 2009 | |
| Cry57Aa1 | ANC87261 | | Noguera & Ibarra | 2009 | Bt kim | | |
| Cry58Aa1 | ANC87260 | | Noguera & Ibarra | 2009 | Bt entomocidus | | |
| Cry59Aa1 | ACR43758 | | Noguera & Ibarra | 2009 | Bt kim LBIT-980 | | |

| | | | | | | | |
|---|---|---|---|---|---|---|---|
| Vip3Aa1 | Vip3Aa | | AAC37036 | Estruch et al | 1996 | PNAS 93, 5389-5394 | AB88 | |
| Vip3Aa2 | Vip3Ab | | AAC37037 | Estruch et al | 1996 | PNAS 93, 5389-5394 | AB424 | |
| Vip3Aa3 | Vip3Ac | | | Estruch et al | 2000 | U.S. Pat. No. 6,137,033 October 2000 | | |
| Vip3Aa4 | PS36A Sup | | AAR81079 | Feitelson et al | 1998 | U.S. Pat. No. 6,656,908 December 2003 | Bt PS36A | WO9818932(A2, A3) 7 May 1998 |
| Vip3Aa5 | PS81F Sup | | AAR81080 | Feitelson et al | 1998 | U.S. Pat. No. 6,656,908 December 2003 | Bt PS81F | WO9818932(A2, A3) 7 May 1998 |
| Vip3Aa6 | Jav90 Sup | | AAR81081 | Feitelson et al | 1998 | U.S. Pat. No. 6,656,908 December 2003 | Bt | WO9818932(A2, A3) 7 May 1998 |
| Vip3Aa7 | Vip83 | | AAK95326 | Cai et al | 2001 | unpublished | Bt YBT-833 | |
| Vip3Aa8 | Vip3A | | AAK97481 | Loguercio et al | 2001 | unpublished | Bt HD125 | |
| Vip3Aa9 | VipS | | CAA76665 | Selvapandiyan et al | 2001 | unpublished | Bt A13 | |
| Vip3Aa10 | Vip3V | | AAN60738 | Doss et al | 2002 | Protein Expr. Purif. 26, 82-88 | Bt | |
| Vip3Aa11 | Vip3A | | AAR36859 | Liu et al | 2003 | unpublished | Bt C9 | |
| Vip3Aa12 | Vip3A-WB5 | | AAM22456 | Wu and Guan | 2003 | unpublished | Bt | |
| Vip3Aa13 | Vip3A | | AAL69542 | Chen et al | 2002 | Sheng Wu Gong Cheng Xue Bao 18, 687-692 | Bt S184 | |
| Vip3Aa14 | Vip | | AAQ12340 | Polumetla et al | 2003 | unpublished | Bt tolworthi | |
| Vip3Aa15 | Vip3A | | AAP51131 | Wu et al | 2004 | unpublished | Bt WB50 | |
| Vip3Aa16 | Vip3LB | | AAW65132 | Mesrati et al | 2005 | FEMS Micro Lett 244, 353-358 | Bt | |
| Vip3Aa17 | Jav90 | | | Feitelson et al | 1999 | U.S. Pat. No. 6,603,063 August 2003 | Javelin 1990 | WO9957282(A2, A3) 11 Nov. 1999 |
| Vip3Aa18 | | | AAX49395 | Cai and Xiao | 2005 | unpublished | Bt 9816C | |
| Vip3Aa19 | Vip3ALD | | DQ241674 | Liu et al | 2006 | unpublished | Bt AL | |
| Vip3Aa19 | Vip3A-1 | | DQ539887 | Hart et al | 2006 | unpublished | | |
| Vip3Aa20 | Vip3A-2 | | DQ539888 | Hart et al | 2006 | unpublished | | |
| Vip3Aa21 | Vip | | ABD84410 | Panbangred | 2006 | unpublished | Bt aizawai | |
| Vip3Aa22 | Vip3A-LS1 | | AAY41427 | Lu et al | 2005 | unpublished | Bt LS1 | |
| Vip3Aa23 | Vip3A-LS8 | | AAY41428 | Lu et al | 2005 | unpublished | Bt LS8 | |
| Vip3Aa24 | | | BI 880913 | Song et al | 2007 | unpublished | Bt WZ-7 | |
| Vip3Aa25 | | | EF608501 | Hsieh et al | 2007 | unpublished | | |
| Vip3Aa26 | | | EU294496 | Shen and Guo | 2007 | unpublished | Bt TF9 | |
| Vip3Aa27 | | | EU332167 | Shen and Guo | 2007 | unpublished | Bt 16 | |
| Vip3Aa28 | | | FJ494817 | Xiumei Yu | 2008 | unpublished | Bt JF23-8 | |
| Vip3Aa29 | | | FJ626674 | Xieumei et al | 2009 | unpublished | Bt JF21-1 | |
| Vip3Aa30 | | | FJ626675 | Xieumei et al | 2009 | unpublished | MD2-1 | |
| Vip3Aa31 | | | FJ626676 | Xieumei et al | 2009 | unpublished | JF21-1 | |
| Vip3Aa32 | | | FJ626677 | Xieumei et al | 2009 | unpublished | MD2-1 | |
| Vip3Ab1 | Vip3B | | AAR40284 | Feitelson et al | 1999 | U.S. Pat. No. 6,603,063 August 2003 | Bt KB59A4-6 | WO9957282(A2, A3) 11 Nov. 1999 |
| Vip3Ab2 | Vip3D | | AAY88247 | Feng and Shen | 2006 | unpublished | Bt | |
| Vip3Ac1 | PS49C | | | Narva et al | . | US application 20040128716 | | |
| Vip3Ad1 | PS158C2 | | | Narva et al | . | US application 20040128716 | | |
| Vip3Ad2 | ISP3B | | CAI43276 | Van Rie et al | 2005 | unpublished | Bt | |
| Vip3Ae1 | ISP3C | | CAI43277 | Van Rie et al | 2005 | unpublished | Bt | |

| Vip3Af1 | ISP3A | CAI43275 | Van Rie et al | 2005 | unpublished | Bt |
| Vip3Af2 | Vip3C | ADN08753 | Syngenta | . | WO 03/075655 | |
| Vip3Ag1 | Vip3B | ADN08758 | Syngenta | . | WO 02/078437 | |
| Vip3Ag2 | | FJ556803 | Audtho et al | 2008 | . | Bt |
| Vip3Ah1 | Vip3S | DQ832323 | Li and Shen | 2006 | unpublished | Bt |
| Vip3Ba1 | | AAV70653 | Rang et al | 2004 | unpublished | |
| Vip3Bb1 | Vip3Z | ADN08760 | Syngenta | . | WO 03/075655 | |
| Vip3Bb2 | | EF439819 | Akhurst et al | 2007 | | |

We claim:

1. A transgenic plant comprising DNA encoding a Cry1Da insecticidal protein and DNA encoding a Cry1Ca insecticidal protein, wherein said Cry1Ca insecticidal protein comprises SEQ ID NO:1, and said Cry1Da insecticidal protein comprises SEQ ID NO:2, wherein said plant further comprises DNA encoding an insecticidal protein selected from the group consisting of Cry1Fa, Vip3Ab, and Cry1E, wherein said plant is selected from the group consisting of a corn plant and a soybean plant, wherein said Cry1Ca insecticidal protein and said Cry1Da insecticidal protein have a different receptor binding site in fall armyworm gut.

2. A seed of the plant according to claim 1, wherein said seed comprises said DNA encoding said Cry1Da insecticidal protein, said DNA encoding said Cry1Ca insecticidal protein, and said DNA encoding said Cry1Fa insecticidal protein.

3. A plurality of plants, comprising non-Bt refuge plants and a plurality of transgenic plants of claim 1, wherein said refuge plants comprise less than 40% of said plurality of plants, and wherein said plurality of plants comprises at least one refuge plant.

4. The plurality of plants of claim 3, wherein said refuge plants comprise less than 30% of said plurality of plants.

5. The plurality of plants of claim 3, wherein said refuge plants comprise less than 20% of said plurality of plants.

6. The plurality of plants of claim 3, wherein said refuge plants comprise less than 10% of said plurality of plants.

7. The plurality of plants of claim 3, wherein said refuge plants comprise less than 5% of said plurality of plants.

8. The plurality of plants of claim 3, wherein said refuge plants are in blocks or strips.

9. A mixture of seeds comprising refuge seeds from non-Bt refuge plants, and a plurality of seeds of claim 2, wherein said refuge seeds comprise less than 40% of all the seeds in the mixture.

10. The mixture of seeds of claim 9, wherein said refuge seeds comprise less than 30% of all the seeds in the mixture.

11. The mixture of seeds of claim 9, wherein said refuge seeds comprise less than 20% of all the seeds in the mixture.

12. The mixture of seeds of claim 9, wherein said refuge seeds comprise less than 10% of all the seeds in the mixture.

13. The mixture of seeds of claim 9, wherein said refuge seeds comprise less than 5% of all the seeds in the mixture.

14. A method of managing development of resistance by a fall armyworm (*Spodoptera frugiperda*) insect to an insecticidal protein derived from a *Bacillus thuringiensis*, said method comprising planting seeds to produce the transgenic plant of claim 1, and contacting said transgenic plant with said fall armyworm.

15. The plurality of plants of claim 3, wherein said plants occupy more than 10 acres.

16. The transgenic plant of claim 1, wherein said transgenic plant is a maize plant.

17. A plant cell of the transgenic plant of claim 1, wherein said plant cell comprises said DNA encoding said Cry1Ca insecticidal protein, said DNA encoding said Cry1Da insecticidal protein, and said DNA encoding said Cry1Fa insecticidal protein.

18. The transgenic plant of claim 1, said plant further comprising DNA encoding a fourth insecticidal protein, said fourth protein being selected from the group consisting of Cry2A and Cry1Ab.

* * * * *